(12) United States Patent
Allis et al.

(10) Patent No.: US 8,404,458 B2
(45) Date of Patent: Mar. 26, 2013

(54) HISTONE MODIFICATIONS AS BINARY SWITCHES CONTROLLING GENE EXPRESSION

(75) Inventors: C. David Allis, New York, NY (US);
Wolfgang Fischle, New York, NY (US);
Holger Dormann, New York, NY (US)

(73) Assignee: The Rockefeller University, New York, NY (US)

( * ) Notice: Subject to any disclaimer, the term of this patent is extended or adjusted under 35 U.S.C. 154(b) by 99 days.

(21) Appl. No.: 10/571,648

(22) PCT Filed: Sep. 15, 2004

(86) PCT No.: PCT/US2004/030161
§ 371 (c)(1),
(2), (4) Date: Apr. 11, 2007

(87) PCT Pub. No.: WO2005/028620
PCT Pub. Date: Mar. 31, 2005

(65) Prior Publication Data
US 2007/0274912 A1    Nov. 29, 2007

Related U.S. Application Data

(60) Provisional application No. 60/503,525, filed on Sep. 16, 2003.

(51) Int. Cl.
*G01N 33/573* (2006.01)
*C07K 14/435* (2006.01)
*C12N 9/12* (2006.01)
(52) U.S. Cl. ............ 435/7.4; 436/86; 530/352; 435/194
(58) Field of Classification Search .................. 435/7.4, 435/194; 436/86; 530/352
See application file for complete search history.

(56) References Cited

U.S. PATENT DOCUMENTS

| 6,362,317 B1 * | 3/2002 | Bonner et al. ............. 530/387.1 |
| 8,020,090 B2 | 9/2011 | Chen et al. |
| 2002/0081638 A1 | 6/2002 | Jenuwein |

FOREIGN PATENT DOCUMENTS

WO    WO 03004050 A1 *    1/2003

OTHER PUBLICATIONS

Fischle et al., "A Binary 'Methyl-Phos Switch' Regulates Binding and Release of HP1 to Histone H3," Posterboard Presentation, Cold Spring Harbor Sympsium on Quantitative Biology (Jun. 2004).
Fischle et al., "Binary Switches and Modification Cassettes in Histone Biology and Beyond," Nature 425:475-9 (2003).

(Continued)

*Primary Examiner* — Rosanne Kosson
(74) *Attorney, Agent, or Firm* — LeClairRyan, a Professional Corporation

(57) ABSTRACT

The present invention relates to a method of modulating a chromatin binding protein or complex which binds to a functional group on an amino acid of a histone. This method involves phosphorylating or dephosphorylating a serine or threonine on the histone proximate to the amino acid under conditions effective to modulate the chromatin binding protein or complex. This method is particularly useful in treating or preventing cancer in a subject. In addition, the histone comprising a serine or threonine proximate to an amino acid capable of binding to a functional group can be used to screen for compounds which prevent or treat cancer. Also disclosed is an antibody or binding portion thereof raised against a binary switch on a histone comprising a phosphorylated serine or threonine proximate to an amino acid bound to a functional group and its use in detecting a condition mediated by that switch.

5 Claims, 20 Drawing Sheets

OTHER PUBLICATIONS

Fischle et al., "Histone and Chromatin Cross-Talk," Current Opinion in Cell Biology 15:172-83 (2003).

Lachner et al., "Methylation of Histone H3 Lysine 9 Creates a Binding Site for HP1 Proteins," Nature 410:116-20 (2001).

Prigent et al., "Phosphorylation of Serine 10 in Histone H3, What For?," Journal of Cell Science 116:3677-85 (2003).

Rea et al., "Regulation of Chromatin Structure by Site-Specific Histone H3 Methyltransferases," Nature 406:593-9 (2000).

Wang et al., "Beyond the Double Helix: Writing and Reading the Histone Code," Novartis Foundation Symposium 259:3-21 (2004).

Wang et al., "Linking Covalent Histone Modifications to Epigenetics: The Rigidity and Plasticity of the Marks," Cold Spring Harbor Symposium on Quantitative Biology 69:161-169 (2004).

International Search Report and Written Opinion for corresponding PCT/US04/30161 (Aug. 15, 2005).

* cited by examiner

| Hs | H4 | Ac-NH- | S G R G K G G K G L - - |
|---|---|---|---|
| Hs | H2A.1 | Ac-NH- | S G R G K Q G G K A - - |
| Hs | H2A.Z | NH₂- | A G - G K A G K D S - - |
| Tet | H4 | NH₂- | A G - G K G G K G M - - |

(with modifications: P, Ac, Ac above T371, K372, K373; P above S376; P above S378; Ac, Ac, P above K381, K382, T383)

*FIG. 6B*

| Hs | H4 | Ac-NH- | S G R G K G G - - |
|---|---|---|---|
| Hs | AML1/RUNX1 | - - G R | S G R G K S F - - |
|   |   |   138 |   146 |
| Hs | AML2/RUNX3 | - - G R | S G R G K S F - - |
|   |   |   189 |   193 |
| Hs | AML3/RUNX2 | - - G R | S G R G K S F - - |
|   |   |   142 |   150 |
| Dm | RUNT | - - G R | S G R G K S F - - |
|   |   |   193 |   201 |

*FIG. 6C*

| Dm | H4 | Ac-NH- | T G R G K G G K G L G - - |
|---|---|---|---|
| Dm | Polycomb | *NH₂- | T G R G K G S K G K L - - |
| Hs | NRF1 | - - Y S | T G R G K P G - - |
|   |   | 215 | 223 |
| Hs | MCM4 | - - S H | T G R G K F R - - |
|   |   | 493 | 501 |

NH$_2$-ARTKQTARKSTGGKAPRKQLATKAARKSAP...

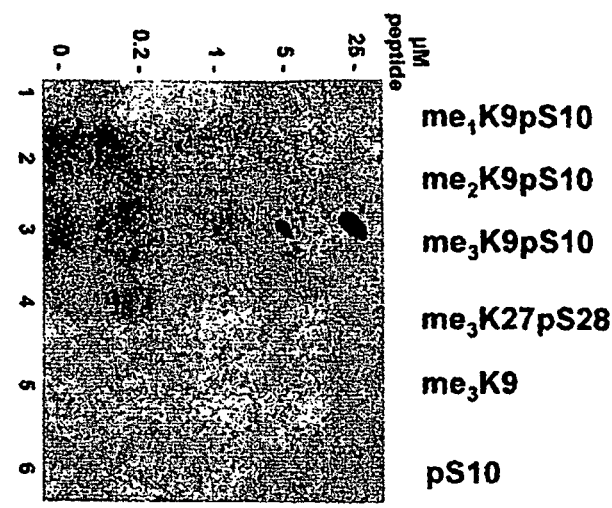
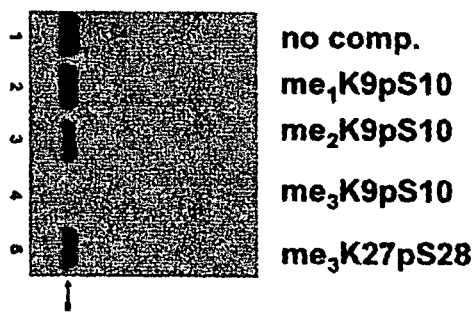
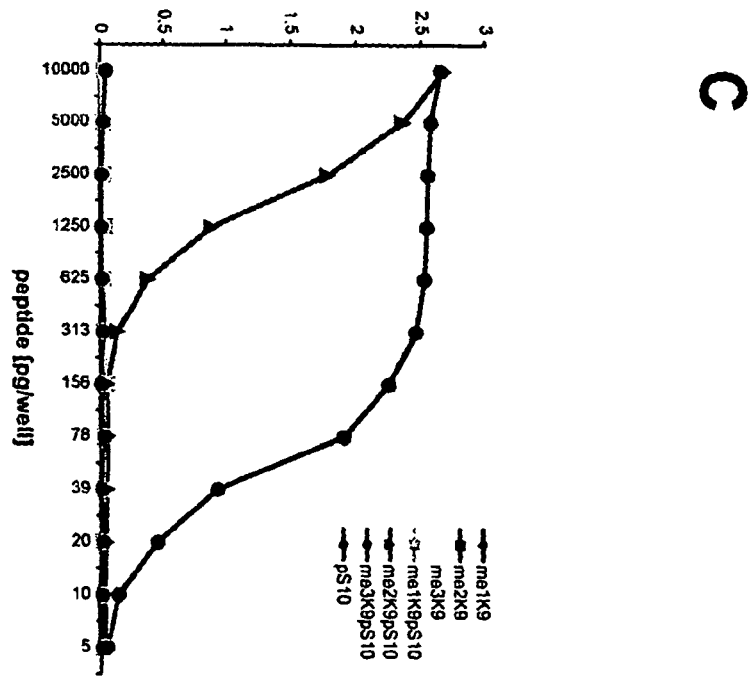
FIGURE 8A-C

6xHIS-HP1β    MKKHHHHHH............... HP1β [CD, aa
10xHIS-HP1β   MGHHHHHHHHHHSSGHIEGRH... HP1β[CD, aa 15-72]

FIGURE 13D

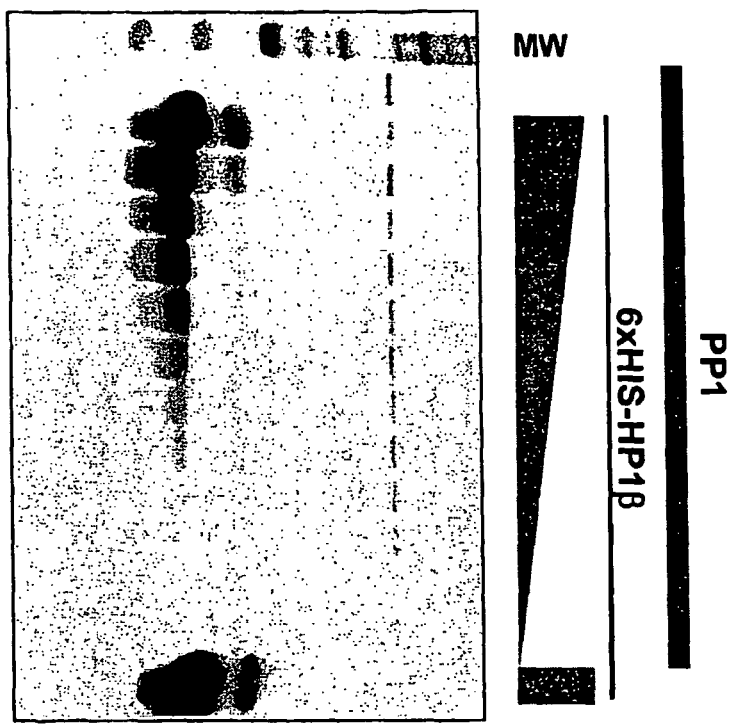
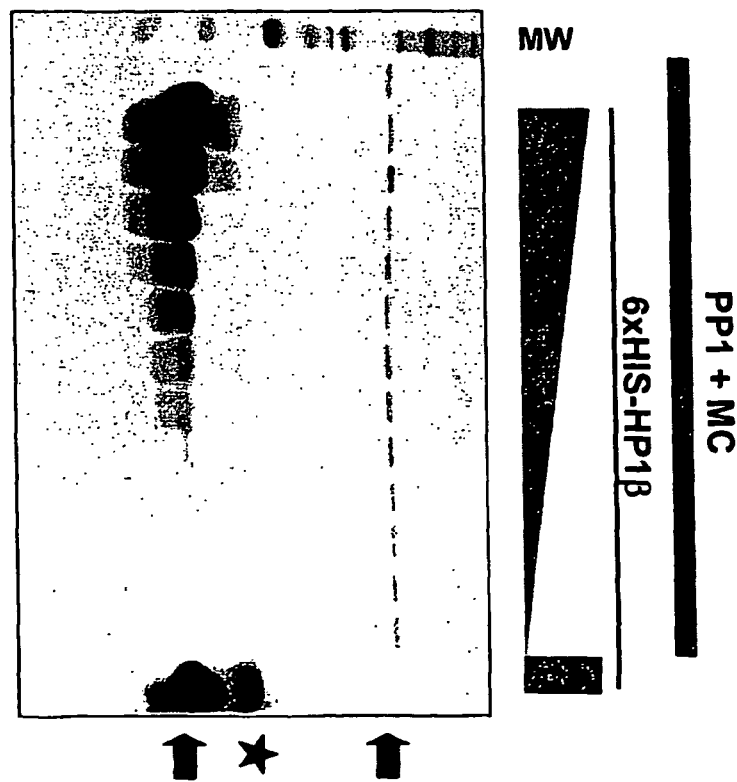
FIGURE 14D

SEQUENCE LISTING

<160> NUMBER OF SEQ ID NOS: 33

<210> SEQ ID NO 1
<211> LENGTH: 39
<212> TYPE: PRT
<213> ORGANISM: Homo sapiens

<400> SEQUENCE: 1

```
Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
                20                  25                  30

Gly Gly Val Lys Lys Pro His
            35
```

<210> SEQ ID NO 2
<211> LENGTH: 26
<212> TYPE: PRT
<213> ORGANISM: Homo sapiens

<400> SEQUENCE: 2

```
Ser Gly Arg Gly Lys Gly Gly Lys Gly Leu Gly Lys Gly Gly Ala Lys
1               5                   10                  15

Arg His Arg Lys Val Leu Arg Asp Asn Ile
                20                  25
```

<210> SEQ ID NO 3
<211> LENGTH: 28
<212> TYPE: PRT
<213> ORGANISM: Homo sapiens

<400> SEQUENCE: 3

```
Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser
                20                  25
```

<210> SEQ ID NO 4
<211> LENGTH: 28
<212> TYPE: PRT
<213> ORGANISM: Homo sapiens

<400> SEQUENCE: 4

```
Ser Gly Arg Gly Lys Gly Gly Lys Gly Leu Gly Lys Gly Gly Ala Lys
1               5                   10                  15

Arg His Arg Lys Val Leu Arg Asp Asn Ile Gln Gly
                20                  25
```

<210> SEQ ID NO 5
<211> LENGTH: 10
<212> TYPE: PRT
<213> ORGANISM: Homo sapiens

<400> SEQUENCE: 5

```
Ser Gly Arg Gly Lys Gly Gly Lys Gly Leu
1               5                   10
```

<210> SEQ ID NO 6
<211> LENGTH: 10
<212> TYPE: PRT
<213> ORGANISM: Homo sapiens

<400> SEQUENCE: 6

```
Ser Gly Arg Gly Lys Gln Gly Gly Lys Ala
1               5                   10
```

<210> SEQ ID NO 7
<211> LENGTH: 9
<212> TYPE: PRT
<213> ORGANISM: Homo sapiens

<400> SEQUENCE: 7

Ala Gly Gly Lys Ala Gly Lys Asp Ser
1               5

<210> SEQ ID NO 8
<211> LENGTH: 9
<212> TYPE: PRT
<213> ORGANISM: Tetrahymena thermophila

<400> SEQUENCE: 8

Ala Gly Gly Lys Gly Gly Lys Gly Met
1               5

<210> SEQ ID NO 9
<211> LENGTH: 13
<212> TYPE: PRT
<213> ORGANISM: Homo sapiens

<400> SEQUENCE: 9

Thr Lys Lys Gly Gln Ser Thr Ser Arg His Lys Lys Thr
1               5                   10

<210> SEQ ID NO 10
<211> LENGTH: 7
<212> TYPE: PRT
<213> ORGANISM: Homo sapiens

<400> SEQUENCE: 10

Ser Gly Arg Gly Lys Gly Gly
1               5

<210> SEQ ID NO 11
<211> LENGTH: 9
<212> TYPE: PRT
<213> ORGANISM: Homo sapiens

<400> SEQUENCE: 11

Gly Arg Ser Gly Arg Gly Lys Ser Phe
1               5

<210> SEQ ID NO 12
<211> LENGTH: 9
<212> TYPE: PRT
<213> ORGANISM: Drosophilia melanogaster

<400> SEQUENCE: 12

Gly Arg Ser Gly Arg Gly Lys Ser Phe
1               5

<210> SEQ ID NO 13
<211> LENGTH: 11
<212> TYPE: PRT
<213> ORGANISM: Drosophilia melanogaster

<400> SEQUENCE: 13

Thr Gly Arg Gly Lys Gly Gly Lys Gly Leu Gly
1               5                   10

<210> SEQ ID NO 14
<211> LENGTH: 11
<212> TYPE: PRT
<213> ORGANISM: Drosophilia melanogaster

<400> SEQUENCE: 14

Thr Gly Arg Gly Lys Gly Ser Lys Gly Lys Leu
1               5                   10

```
<210> SEQ ID NO 15
<211> LENGTH: 9
<212> TYPE: PRT
<213> ORGANISM: Homo sapiens

<400> SEQUENCE: 15

Tyr Ser Thr Gly Arg Gly Lys Pro Gly
1               5

<210> SEQ ID NO 16
<211> LENGTH: 9
<212> TYPE: PRT
<213> ORGANISM: Homo sapiens

<400> SEQUENCE: 16

Ser His Thr Gly Arg Gly Lys Phe Arg
1               5

<210> SEQ ID NO 17
<211> LENGTH: 30
<212> TYPE: PRT
<213> ORGANISM: Homo sapiens

<400> SEQUENCE: 17

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro
            20                  25                  30

<210> SEQ ID NO 18
<211> LENGTH: 15
<212> TYPE: PRT
<213> ORGANISM: Homo sapiens

<400> SEQUENCE: 18

Thr Ala Arg Lys Ser Thr Gly Gly Lys Ala Pro Arg Lys Gln Leu
1               5                   10                  15

<210> SEQ ID NO 19
<211> LENGTH: 51
<212> TYPE: PRT
<213> ORGANISM: Drosophilia melanogaster

<400> SEQUENCE: 19

Asp Leu Val Tyr Ala Ala Glu Lys Ile Ile Gln Lys Arg Val Lys Lys
1               5                   10                  15

Gly Val Val Glu Tyr Arg Val Lys Trp Lys Gly Trp Asn Gln Arg Tyr
            20                  25                  30

Asn Thr Trp Glu Pro Glu Val Asn Ile Leu Asp Arg Arg Leu Ile Asp
        35                  40                  45

Ile Tyr Glu
    50

<210> SEQ ID NO 20
<211> LENGTH: 51
<212> TYPE: PRT
<213> ORGANISM: Drosophilia melanogaster

<400> SEQUENCE: 20

Glu Glu Glu Tyr Ala Val Glu Lys Ile Ile Asp Arg Arg Val Arg Lys
1               5                   10                  15

Gly Lys Val Glu Tyr Tyr Leu Lys Trp Lys Gly Tyr Pro Glu Thr Glu
```

```
                20                  25                  30

Asn Thr Trp Glu Pro Glu Asn Asn Leu Asp Cys Gln Asp Leu Ile Gln
         35                  40                  45

Gln Tyr Glu
     50

<210> SEQ ID NO 21
<211> LENGTH: 51
<212> TYPE: PRT
<213> ORGANISM: Mus musculus

<400> SEQUENCE: 21

Glu Gln Val Phe Ala Ala Glu Cys Ile Leu Ser Lys Arg Leu Arg Lys
1               5                   10                  15

Gly Lys Leu Glu Tyr Leu Val Lys Trp Arg Gly Trp Ser Ser Lys His
                20                  25                  30

Asn Ser Trp Glu Pro Glu Glu Asn Ile Leu Asp Pro Arg Leu Leu Leu
         35                  40                  45

Ala Phe Gln
     50

<210> SEQ ID NO 22
<211> LENGTH: 51
<212> TYPE: PRT
<213> ORGANISM: Homo sapiens

<400> SEQUENCE: 22

Glu His Val Phe Ala Val Glu Ser Ile Glu Lys Arg Ile Arg Lys
1               5                   10                  15

Gly Arg Val Glu Tyr Leu Val Lys Trp Arg Gly Trp Ser Pro Lys Tyr
                20                  25                  30

Asn Thr Trp Glu Pro Glu Glu Asn Ile Leu Asp Pro Arg Leu Leu Ile
         35                  40                  45

Ala Phe Gln
     50

<210> SEQ ID NO 23
<211> LENGTH: 51
<212> TYPE: PRT
<213> ORGANISM: Homo sapiens

<400> SEQUENCE: 23

Glu Arg Val Phe Ala Ala Glu Ser Ile Ile Lys Arg Ile Arg Lys
1               5                   10                  15

Gly Arg Ile Glu Tyr Leu Val Lys Trp Lys Gly Trp Ala Ile Lys Tyr
                20                  25                  30

Ser Thr Trp Glu Pro Glu Glu Asn Ile Leu Asp Ser Arg Leu Ile Ala
         35                  40                  45

Ala Phe Glu
     50

<210> SEQ ID NO 24
<211> LENGTH: 51
<212> TYPE: PRT
<213> ORGANISM: Homo sapiens

<400> SEQUENCE: 24

Glu Gln Val Phe Ala Val Glu Ser Ile Arg Lys Arg Val Arg Lys
1               5                   10                  15

Gly Lys Val Glu Tyr Leu Val Lys Trp Lys Gly Trp Pro Pro Lys Tyr
```

```
                  20                  25                  30

Ser Thr Trp Glu Pro Glu Glu His Ile Leu Asp Pro Arg Leu Val Met
            35                  40                  45

Ala Tyr Glu
    50

<210> SEQ ID NO 25
<211> LENGTH: 51
<212> TYPE: PRT
<213> ORGANISM: Homo sapiens

<400> SEQUENCE: 25

Glu Arg Val Phe Ala Ala Glu Ala Leu Leu Lys Arg Ile Arg Lys
1               5                   10                  15

Gly Arg Met Glu Tyr Leu Val Lys Trp Lys Gly Trp Ser Gln Lys Tyr
            20                  25                  30

Ser Thr Trp Glu Pro Glu Glu Asn Ile Leu Asp Ala Arg Leu Leu Ala
            35                  40                  45

Ala Phe Glu
    50

<210> SEQ ID NO 26
<211> LENGTH: 51
<212> TYPE: PRT
<213> ORGANISM: Homo sapiens

<400> SEQUENCE: 26

Glu Glu Glu Tyr Val Val Glu Lys Val Leu Asp Arg Arg Val Val Lys
1               5                   10                  15

Gly Gln Val Glu Tyr Leu Leu Lys Trp Lys Gly Phe Ser Glu Glu His
            20                  25                  30

Asn Thr Trp Glu Pro Glu Lys Asn Leu Asp Cys Pro Glu Leu Ile Ser
            35                  40                  45

Glu Phe Met
    50

<210> SEQ ID NO 27
<211> LENGTH: 51
<212> TYPE: PRT
<213> ORGANISM: Homo sapiens

<400> SEQUENCE: 27

Glu Glu Glu Tyr Val Val Glu Lys Val Leu Asp Arg Arg Val Val Lys
1               5                   10                  15

Gly Lys Val Glu Tyr Leu Leu Lys Trp Lys Gly Phe Ser Asp Glu Asp
            20                  25                  30

Asn Thr Trp Glu Pro Glu Glu Asn Leu Asp Cys Pro Asp Leu Ile Ala
            35                  40                  45

Glu Phe Leu
    50

<210> SEQ ID NO 28
<211> LENGTH: 51
<212> TYPE: PRT
<213> ORGANISM: Homo sapiens

<400> SEQUENCE: 28

Pro Glu Glu Phe Val Val Glu Lys Val Leu Asp Arg Arg Val Val Asn
1               5                   10                  15

Gly Lys Val Glu Tyr Phe Leu Lys Trp Lys Gly Phe Thr Asp Ala Asp
```

```
                20                  25                  30

Asn Thr Trp Glu Pro Glu Asn Leu Asp Cys Pro Glu Leu Ile Glu
        35                  40                  45

Asp Phe Leu
        50

<210> SEQ ID NO 29
<211> LENGTH: 53
<212> TYPE: PRT
<213> ORGANISM: Homo sapiens

<400> SEQUENCE: 29

Ser Gln Glu Phe Glu Val Glu Ala Ile Val Asp Lys Arg Gln Asp Lys
1               5                   10                  15

Asn Gly Asn Thr Gln Tyr Leu Val Arg Trp Lys Gly Tyr Asp Lys Gln
                20                  25                  30

Asp Asp Thr Trp Glu Pro Glu Gln His Leu Met Asn Cys Glu Lys Cys
        35                  40                  45

Val His Asp Phe Asn
        50

<210> SEQ ID NO 30
<211> LENGTH: 51
<212> TYPE: PRT
<213> ORGANISM: Homo sapiens

<400> SEQUENCE: 30

Leu Tyr Asp Phe Glu Val Glu Tyr Leu Cys Asp Tyr Lys Lys Ile Arg
1               5                   10                  15

Glu Gln Glu Tyr Tyr Leu Val Lys Trp Arg Gly Tyr Pro Asp Ser Glu
                20                  25                  30

Ser Thr Trp Glu Pro Arg Gln Asn Leu Lys Cys Val Arg Ile Leu Lys
        35                  40                  45

Gln Phe His
        50

<210> SEQ ID NO 31
<211> LENGTH: 51
<212> TYPE: PRT
<213> ORGANISM: Homo sapiens

<400> SEQUENCE: 31

Leu Asn Asn Tyr Glu Val Glu Tyr Leu Cys Asp Tyr Lys Val Val Lys
1               5                   10                  15

Asp Met Glu Tyr Tyr Leu Val Lys Trp Lys Gly Trp Pro Asp Ser Thr
                20                  25                  30

Asn Thr Trp Glu Pro Leu Gln Asn Leu Lys Cys Pro Leu Leu Leu Gln
        35                  40                  45

Gln Phe Ser
        50

<210> SEQ ID NO 32
<211> LENGTH: 9
<212> TYPE: PRT
<213> ORGANISM: Artificial
<220> FEATURE:
<223> OTHER INFORMATION: 6xHIS-HP1Beta Tag

<400> SEQUENCE: 32

Met Lys Lys His His His His His His
1               5
```

```
<210> SEQ ID NO 33
<211> LENGTH: 21
<212> TYPE: PRT
<213> ORGANISM: Artificial
<220> FEATURE:
<223> OTHER INFORMATION: 10xHIS-HP1Beta Tag

<400> SEQUENCE: 33

Met Gly His His His His His His His His His Ser Ser Gly His
1               5                   10                  15

Ile Glu Gly Arg His
            20
```

HISTONE MODIFICATIONS AS BINARY SWITCHES CONTROLLING GENE EXPRESSION

This application claims the benefit of U.S. Provisional Patent Application Ser. No. 60/503,525, filed Sep. 16, 2003, which is hereby incorporated by reference in its entirety.

FIELD OF THE INVENTION

The present invention relates to histone modifications as binary switches and their use for controlling gene expression.

BACKGROUND OF THE INVENTION

Within the eukaryotic cell nucleus, genetic information is organized in a highly conserved structural polymer, termed chromatin, which supports and controls the crucial functions of the genome. The chromatin template undergoes dynamic changes during many genetic processes. These include necessary structural reorganizations that occur during DNA replication and cell cycle progression, spatially and temporally coordinated gene expression, as well as DNA repair and recombination events. The fundamental repeating unit of chromatin is the nucleosome, which consists of 146 base pairs of DNA wrapped around an octamer of core histone proteins, H2A, H2B, H3, and H4. Linker histones of the H1 class associate with DNA between single nucleosomes, establishing a higher level of organization, the so-called 'solenoid' helical or zig-zag fibers (30 nm fibers). Chromatin architecture beyond the 30 nm fibers is less clear, but folding and unfolding of putative superstructures is thought to have a pronounced impact on genomic function and gene activity.

Core histone proteins are evolutionary conserved and consist mainly of flexible N-terminal tails protruding outward from the nucleosome, and globular C-terminal domains making up the nucleosome scaffold. Histones function as acceptors for a variety of post-translational modifications, including acetylation, methylation and ubiquitination of lysine (K) residues, phosphorylation of serine (S) and threonine (T) residues, and methylation of arginine (R) residues (FIG. 1A). The different histone modifications and the corresponding enzymatic systems that maintain them have been reviewed extensively in the recent literature (e.g. Zhang et al., "Transcription Regulation by Histone Methylation: Interplay Between Different Covalent Modifications of the Core Histone Tails," *Genes Dev* 15:2343-2360 (2000); Kouzarides, "Histone Methylation in Transcriptional Control," *Curr Opin Genet Dev* 12:198-209 (2002); Lachner et al., "The Many Faces of Histone Lysine Methylation," *Curr Opin Cell Biol* 14:286-298 (2002); Berger, Histone Modifications in Transcriptional Regulation," *Curr Opin Genet Dev* 12:142-148 (2002); and Eberharter et al., "Histone Acetylation: A Switch Between Repressive and Permissive Chromatin," Second in Review Series on Chromatin Dynamics. *EMBO Rep* 3:224-229 (2002)). Combinations of post-translational marks on single histones, single nucleosomes and nucleosomal domains establish local and global patterns of chromatin modification that may specify unique downstream functions (Strahl et al., "The Language of Covalent Histone Modifications," *Nature* 403:41-45 (2000); Turner, "Histone Acetylation and an Epigenetic Code," *Bioessays* 22:836-845 (2000)). These patterns can be altered by multiple extracellular and intracellular stimuli, and chromatin itself has been proposed to serve as signaling platform and to function as a genomic integrator of various signaling pathways (Cheung et al., "Signaling to Chromatin Through Histone Modifications," *Cell* 103:263-271 (2000)).

One major challenge in chromatin biology is connecting particular modifications with distinct biological functions and vice versa. One of the better-understood histone modifications in that aspect is histone acetylation. It is now generally accepted that hyperacetylated histones are mostly associated with activated genomic regions, at both local and global levels. In contrast, deacetylation (leading to hypoacetylation) mainly results in repression and silencing (Turner, "Histone Acetylation and an Epigenetic Code," *Bioessays* 22:836-845 (2000) and Grunstein, "Histone Acetylation in Chromatin Structure and Transcription," *Nature* 389:349-352 (1997)). Interestingly, histone methylation appears to have multiple effects on chromatin function in a system- and site-specific manner. Methylation of H3 on K9, for example, is largely associated with silencing and repression in many species. Methylation of H3 on K4, on the other hand, is most often associated with active or permissive chromatin regions. However, deletion of the H3-K4 HMT, Set1, in budding yeast causes defects in rDNA silencing (Briggs et al., "Histone H3 Lysine 4 Methylation is Mediated by Set1 and Required for Cell Growth and rDNA Silencing in *Saccharomyces cerevisiae*," *Genes Dev* 15:3286-3295 (2001) and Bryk et al., "Evidence that Set1, a Factor Required for Methylation of Histone H3, Regulates rDNA Silencing in *S. cerevisiae* by a Sir2-independent Mechanism," *Curr Biol* 12:165-170 (2002)). These findings raise the question of whether methylation of H3 on K4 is also involved in gene repression in this organism. Similarly, methylation of H3-K36 has been suggested to be involved in transcriptional repression (Strahl et al., "Set2 is a Nucleosomal Histone H3-selective Methyltransferase that Mediates Transcriptional Repression," *Mol Cell Biol* 22:1298-1306 (2002)), but the corresponding modifying enzyme, Set2, has been found in complex with actively transcribing (or elongation engaged) RNA PolII (Li et al., "Association of the Histone Methyltransferase Set2 with RNA Polymerase II Plays a Role in Transcription Elongation," *J Biol Chem* 14:14 (2002)). Along with the dual personality of the phosphorylation of H3 at S10, which has been implicated in transcriptional activation, but also mitotic chromosome condensation (Cheung et al., "Synergistic Coupling of Histone H3 Phosphorylation and Acetylation in Response to Epidermal Growth Factor Stimulation," *Mol Cell* 5:905-915 (2000)), these results argue that single histone modifications may have distinct biological effects depending on their context.

The findings that a particular post-translational modification might mediate separate, and sometimes opposing, physiological processes led to the suggestion that multiple readouts of a certain covalent mark could be obtained by various combinations of different modifications in the same chromatin region (Strahl et al., "The Language of Covalent Histone Modifications," *Nature* 403:41-45 (2000) and Jenuwein et al., "Translating the Histone Code," *Science* 293:1074-1080 (2001)). Indeed, the use of antibodies that recognize such combinations of post-translational marks, and the more recent application of novel mass spectrometry approaches, have verified that particular sets of modifications might occur concomitantly on the same histone tail (Cheung et al., "Synergistic Coupling of Histone H3 Phosphorylation and Acetylation in Response to Epidermal Growth Factor Stimulation," *Mol Cell* 5:905-915 (2000); Zhang et al., "Histone Acetylation and Deacetylation: Identification of Acetylation and Methylation Sites of HeLa Histone H4 by Mass Spectrometry," *Mol Cell Proteomics* 1:500-508 (2002); and Zhang et al., "Identification of Acetylation and Methylation Sites of Histone H3 from Chicken Erythrocytes by High-Accuracy Matrix-Assisted Laser Desorption Ionization-Time-of-Flight, Matrix-Assisted Laser Desorption Ionization-Post-source Decay, and Nanoelectrospray Ionization Tandem Mass Spectrometry," *Anal Biochem* 306:259-269 (2002)). While the field is far away from deciphering the specific modification patterns at the level of single histones, single nucleosomes, and nucleosomal domains, mounting evidence suggests that different histone modifications can influence or 'communicate' with each other on several levels.

An ever-growing number of modification sites on both histone-tail and non-tail domains have been identified (for reference see FIG. 1 and (Zhang et al., "Transcription Regulation by Histone Methylation: Interplay Between Different Covalent Modifications of the Core Histone Tails," *Genes Dev* 15:2343-2360 (2000))). Whereas serine and threonine residues are well-known phospho-acceptor sites, lysine and arginine residues have multiple choices of post-translational modification possibilities (FIG. 1A). For example, lysine residues in histones can be modified by acetylation, monoubiquitination or mono-, di-, and tri-methylation. Similarly, arginines might be mono- or di-methylated (symmetric or asymmetric) (Zhang et al., "Transcription Regulation by Histone Methylation: Interplay Between Different Covalent Modifications of the Core Histone Tails," *Genes Dev* 15:2343-2360 (2000) and Bannister et al., "Histone Methylation: Dynamic or Static?," *Cell* 109:801-806 (2002)). While it remains unclear as to what extent, if at all, individual residues undergo 'choices' of modification, it is well documented that H3-K9 and H3-K14 can be either acetylated or (mono-, di-, tri-) methylated (Zhang et al., "Histone Acetylation and Deacetylation: Identification of Acetylation and Methylation Sites of HeLa Histone H4 by Mass Spectrometry," *Mol Cell Proteomics* 1:500-508 (2002) and Zhang et al., "Identification of Acetylation and Methylation Sites of Histone H3 from Chicken Erythrocytes by High-Accuracy Matrix-Assisted Laser Desorption Ionization-Time-of-Flight, Matrix-Assisted Laser Desorption Ionization—Post-source Decay, and Nanoelectrospray Ionization Tandem Mass Spectrometry," *Anal Biochem* 306:259-269 (2002)). Obviously, different marks on the same site cannot co-exist, and, therefore, they exclude each other. An acetyl group, for example, must be removed before a methyl group can be added and complexes that contain both, HDACs and HMTs, have now been identified (Czermin et al., "Physical and Functional Association of SU(VAR)3-9 and HDAC1 in *Drosophila*," *EMBO Rep* 2:915-919 (2001); Vaute et al., "Functional and Physical Interaction Between the Histone Methyl Transferase Suv39H1 and Histone Deacetylases," *Nucleic Acids Res* 30:475-481 (2002); and Zhang et al., "Association of Class II Histone Deacetylases with Heterochromatin Protein 1: Potential Role for Histone Methylation in Control of Muscle Differentiation," *Mol Cell Biol* 22:7302-7312 (2002)). Genetic studies in *Schizosaccharomyces pombe* have further shown that the HDAC, Clr6, is necessary for methylation at H3-K9 by the Clr4 HMT to occur (Nakayama et al., "Role of Histone H3 Lysine 9 Methylation in Epigenetic Control of Heterochromatin Assembly," *Science* 292:110-113 (2001)).

It seems obvious that different modifications of a particular site can have different readouts and biological functions. Nevertheless, it is now known that the exact state of methylation (i.e. mono-, di- and tri-methylation) of a single lysine residue has an impact on physiological processes. For example, it was recently shown, that di-methylation of H3-K4 occurs at both inactive and active euchromatic genes, whereas tri-methylation is present exclusively at active genes (Santos-Rosa et al., "Active Genes are Tri-methylated at K4 of Histone H3," *Nature* 419:407-411 (2002)). Similar studies investigating other sites of methylation are underway, and it will be interesting to see what additional layers of complexity will be added to histone modifications by the modification choice of a single residue.

Many of the enzymes that post-translationally modify histones display not only a high degree of specificity towards a particular site, but also towards the pre-existing modification-state of their substrate. So far the N-terminal tail of H3 has the highest density of post-translational modifications mapped among all histones, and a complex matrix of putative combinations of marks is emerging (FIG. 1B). Methylation on H3-K9, for example, appears to trigger sequential events leading ultimately to transcriptional repression (Wang et al., "Purification and Functional Characterization of a Histone H3-lysine 4-Specific Methyltransferase," *Mol Cell* 8:1207-1217 (2001)). At least in vitro, this mark can inhibit acetylation of the H3 tail (on K14, K18, and K23) by HATs (e.g., p300) (Wang et al., "Purification and Functional Characterization of a Histone H3-lysine 4-Specific Methyltransferase," *Mol Cell* 8:1207-1217 (2001)), and methylation of H3 on K4 by HMTs (e.g., Set7) (Wang et al., "Purification and Functional Characterization of a Histone H3-lysine 4-Specific Methyltransferase," *Mol Cell* 8:1207-1217 (2001)). In contrast, H3-K4 methylation inhibits K9 methylation by Su(var)3-9, but promotes acetylation of H3 by p300 (Wang et al., "Purification and Functional Characterization of a Histone H3-lysine 4-Specific Methyltransferase," *Mol Cell* 8:1207-1217 (2001)).

Remarkably, the choice of methylation of H3 on K9 could be dictated by H3-S10 phosphorylation. In mammalian cells, this mark not only inhibits methylation on K9 (Rea et al., "Regulation of Chromatin Structure by Site-specific Histone H3 Methyltransferases," *Nature* 406:593-599 (2000)), but also precedes and promotes acetylation on K14 following specific signals (Cheung et al., "Synergistic Coupling of Histone H3 Phosphorylation and Acetylation in Response to Epidermal Growth Factor Stimulation," *Mol Cell* 5:905-915 (2000)), see also (Cheung et al., "Signaling to Chromatin Through Histone Modifications," *Cell* 103:263-271 (2000)) and references therein). In *Saccharomyces cerevisiae*, Sfl1 and Gcn5, the enzymes that phosphorylate H3-S10 and acetylate H3-K14, respectively, appear to work synergistically to mediate gene activation (Lo et al., "Snf1—A Histone Kinase That Works in Concert with the Histone Acetyltransferase Gcn5 to Regulate Transcription," *Science* 293:1142-1146 (2001)). Moreover, acetylation on H3-K9 and H3-K14 stimulates methylation of H3-K4 by the HMT, MLL (for mixed lineage leukemia protein) (Milne et al., "MLL Targets SET Domain Methyltransferase Activity to Hox gene Promoters," *Mol Cell* 10:1107-1117 (2002)). This result is consistent with the enrichment of histones carrying these modifications on HOX gene promoters as shown by ChIP assays (Milne et al., "MLL Targets SET Domain Methyltransferase Activity to Hox gene Promoters," *Mol Cell* 10:1107-1117 (2002)). Conversely, methylation on H3-K4 itself can stimulate the subsequent acetylation of H3 (as discussed above). In vitro, further interplay is seen at the level of H3-S10 phosphorylation by the mitotic kinase Ipl1/aurora, which is stimulated when H3-K9 and H3-K14 are acetylated (Rea et al., "Regulation of Chromatin Structure by Site-specific Histone H3 Methyltransferases," *Nature* 406:593-599 (2000)).

Additional tail-restricted cross-talk is emerging from studies on modifications of H4 (FIG. 1C). Methylation of H4-R3 by PRMTI, for example, is heavily impaired by acetylation of H4 on K5, K8, K12, and K16 (Wang et al., "Methylation of Histone H4 at Arginine 3 Facilitating Transcriptional Activation by Nuclear Hormone Receptor," *Science* 293:853-857 (2001)). In contrast, acetylation of H4 on K8 and K12 by the HAT p300 is elevated after methylation of R3 (Wang et al., "Methylation of Histone H4 at Arginine 3 Facilitating Transcriptional Activation by Nuclear Hormone Receptor," *Science* 293:853-857 (2001)). Also, it has been suggested that methylation of K20 and acetylation of K16 are mutually exclusive to each other (Nishioka et al., "PR-Set7 is a Nucleosome-specific Methyltransferase that Modifies Lysine 20 of Histone H4 and is Associated with Silent Chromatin," *Mol Cell* 9:1201-1213 (2002)). The local cross-talk situation is likely to be more complicated in vivo, and enzymes that modify the same site might be influenced differently by the modification-state of their substrate.

Perhaps more fascinating than the direct synergism/antagonism or 'communication' of adjacent modifications in the same histone tail ('cis' effects) is the unexpected discovery that modifications on different histones can affect each other ('trans' effects) (Wang et al., "Purification and Functional Characterization of a Histone H3-lysine 4-Specific Methyltransferase," *Mol Cell* 8:1207-1217 (2001); Sun et al., "Ubiquitination of Histone H2B Regulates H3 Methylation and Gene Silencing in Yeast," *Nature* 418:104-108 (2002); Briggs et al., "Gene Silencing: Trans-histone Regulatory Pathway in Chromatin," *Nature* 418:498 (2002); Dover et al., "Methylation of Histone H3 by COMPASS Requires Ubiquitination of Histone H2B by Rad6," *J Biol Chem* 277:28368-28371 (2002); and Ng et al., "Ubiquitination of Histone H2B by Rad6 is Required for Efficient Dot1-Mediated Methylation of Histone H3 Lysine 79," *J Biol Chem* 277:34655-34657 (2002)). These effects might be restricted to a single nucleosome or might affect larger nucleosomal arrays or domains (FIG. 2). For example, in vitro studies using p300 showed that this HAT acetylates both H3 and H4 especially in nucleosomes where H3 is methylated on K4 (Wang et al., "Purification and Functional Characterization of a Histone H3-lysine 4-Specific Methyltransferase," *Mol Cell* 8:1207-1217 (2001)). In contrast, methylation of H3 on K9 significantly inhibits the activity of p300 towards nucleosomal histones, H3 as well as H4 (Wang et al., "Purification and Functional Characterization of a Histone H3-lysine 4-Specific Methyltransferase," *Mol Cell* 8:1207-1217 (2001)).

Another intriguing 'trans' cross-talk originates from work in *Saccharomyces cerevisiae* linking ubiquitination of H2B to methylation of H3 (FIG. 2A) (Sun et al., "Ubiquitination of Histone H2B Regulates H3 Methylation and Gene Silencing in Yeast," *Nature* 418:104-108 (2002); Briggs et al., "Gene Silencing: Trans-histone Regulatory Pathway in Chromatin," *Nature* 418:498 (2002); Dover et al., "Methylation of Histone H3 by COMPASS Requires Ubiquitination of Histone H2B by Rad6," *J Biol Chem* 277:28368-28371 (2002); and Ng et al., "Ubiquitination of Histone H2B by Rad6 is Required for efficient Dot1-Mediated Methylation of Histone H3 Lysine 79," *J Biol Chem* 277:34655-34657 (2002)). Ubiquitination of H2A and H2B in mammalian cells had been known for a long time (e.g. ubiquitin was discovered on H2A (Goldknopf et al., "Isolation and Characterization of Protein A24, a "Hitone-like" Non-histone Chromosomal Protein," *Journal of Biological Chemistry* 250:7182-7187 (1975)), but without an obvious link to protein turnover, the consequences and functions of histone monoubiquitination had been elusive. With the discovery of monoubiquitination of H2B in yeast, genetic studies of histone ubiquitination became possible (Robzyk et al., "Rad6-dependent Ubiquitination of Histone H2B in Yeast," *Science* 287:501-504 (2000)). Surprisingly, mutagenesis of either the ubiquitin acceptor site, H2B-K123 (equals human H2B-K120), or disruption of the ubiquitin-conjugating enzyme Rad6/Ubc2 in this organism results in a striking loss of methylation at H3-K4 and H3-K79 (Sun et al., "Ubiquitination of Histone H2B Regulates H3 Methylation and Gene Silencing in Yeast," *Nature* 418:104-108 (2002); Briggs et al., "Gene Silencing: Trans-histone Regulatory Pathway in Chromatin," *Nature* 418:498 (2002); Dover et al., "Methylation of Histone H3 by COMPASS Requires Ubiquitination of Histone H2B by Rad6," *J Biol Chem* 277:28368-28371 (2002); and Ng et al., "Ubiquitination of Histone H2B by Rad6 is Required for efficient Dot1-Mediated Methylation of Histone H3 Lysine 79," *J Biol Chem* 277:34655-34657 (2002)). Altogether, these results indicate that ubiquitination of H2B is a prerequisite for methylation of H3 on K4 and K79. On the other hand, abolishment of H3-K4 or H3-K79 methylation has no effect on H2B ubiquitination, suggesting that the cross-talk is unidirectional. This control of a modification pattern in 'trans' is site-specific since another site of methylation of H3 in yeast, K36, is not affected (Briggs et al., "Gene Silencing: Trans-histone Regulatory Pathway in Chromatin," *Nature* 418:498 (2002)) (note: methylation of H3-K27 has not been detected in budding yeast (Cao et al., "Role of Histone H3 Lysine 27 Methylation in Polycomb-group Silencing," *Science* 298:1039-1043 (2002)).

Interestingly, inter-histone cross-talk may not be restricted to a single nucleosome. In yeast, about 5% of H2B is estimated to be ubiquitinated (Sun et al., "Ubiquitination of Histone H2B Regulates H3 Methylation and Gene Silencing in Yeast," *Nature* 418:104-108 (2002) and Robzyk et al., "Rad6-dependent Ubiquitination of Histone H2B in Yeast," *Science* 287:501-504 (2000)), about 35% of the total H3 pool is thought to be methylated on K4 (Sun et al., "Ubiquitination of Histone H2B Regulates H3 Methylation and Gene Silencing in Yeast," *Nature* 418:104-108 (2002)), and 90% of all H3 is methylated on K79 (van Leeuwen et al., "Dot1p Modulates Silencing in Yeast by Methylation of the Nucleosome Core," *Cell* 109:745-756 (2002)). Since ubiquitination of H2B appears to be far sub-stochiometric to the methylation of H3, the newly discovered control mechanism might serve as a paradigm for 'master control switches' directing the modification pattern of a whole nucleosomal region (FIG. 2B).

Another remarkable feature about this 'trans-communication' is the cross-talk between distinct regions of the histone proteins: the N-terminal tail (H3-K4), the histone core region (H3-K79) and the C-terminal tail (H2B-K123) (see FIG. 2A). So far, methylation on H3-K79 is the only known site of modification identified that lies within the nucleosome core domain (see FIG. 1B and (van Leeuwen et al., "Dot1p Modulates Silencing in Yeast by Methylation of the Nucleosome Core," *Cell* 109:745-756 (2002) and Ng et al., "Lysine Methylation Within the Globular Domain of Histone H3 by Dot1 is Important for Telomeric Silencing and Sir Protein Association," *Genes Dev* 16:1518-1527 (2002)). However, additional sites of modification in the globular region of H3 or other core histones may exist. Genetic studies in *Saccharomyces cerevisiae*, for example, have identified two patches of sequence in the globular regions of H3 and H4 that are crucial for gene silencing mechanisms and heterochromatin formation (Park et al., "A Core Nucleosome Surface Crucial for Transcriptional Silencing," *Nat Genet* 32:273-279 (2002)). In the crystal structure of the nucleosome, these regions are located at the H3/H4 histone-fold motif centered around H3-K79 (see FIGS. 1B and 1C). Whether other, yet unknown, modifications in these patches provide additional cross-talk for the establishment of distinct chromatin readouts is an intriguing possibility.

Besides cross-talk between different covalent modifications, another way of 'communication' within the nucleosome core could be disulfide bond-mediated dimerization. It may not be a coincidence that H3 is the only core histone containing a single cysteine (C110), which is conserved in all species except for budding yeast. Formation of a disulfide bond between the two H3 molecules of each nucleosome might place severe conformational restraints on the structure of individual nucleosomes, nucleosomal arrays or chromosomal domains (see FIGS. 1B and 2A for the positioning of C110 within H3 and a nucleosome, respectively). Early pioneering studies using iodoacetamide labeling have indicated that disulfide-linkage of H3 via C110 correlates with transcriptional silencing (Prior et al., "Reversible Changes in Nucleosome Structure and Histone H3 Accessibility in Transcriptionally Active and Inactive States of rDNA Chromatin," *Cell* 34:1033-1042 (1983)). Nucleosomes in active regions, in contrast, might be actively maintained in a more reduced, and presumably more open, state. Such reduced regions overlap with hyperacetylated nucleosomes as indicated by mercury-column chromatography (Chen-Cleland et al., Recovery of Transcriptionally Active Chromatin Restriction Fragments by Binding to Organomercurial-agarose Magnetic Beads. A Rapid and Sensitive Method for Monitoring Changes in Higher Order Chromatin Structure During Gene Activation and Repression," *J Biol Chem* 268:23409-23416 (1993)).

Singular as well as combinatorial histone modifications obviously impact on chromatin organization and structure. How is a specific modification pattern then translated into changes in genome status and activity? Modifications could directly interfere with the integrity and stability of a single nucleosome or an array of nucleosomes. Bulk acetylation, for example, has been shown to (i) alter the secondary structure of the histone tail, (ii) weaken histone tail-DNA interactions, and (iii) reduce internucleosomal interactions and chromatin folding (see (Annunziato et al., "Role of Histone Acetylation in the Assembly and Modulation of Chromatin Structures," *Gene Expr* 9:37-61 (2000)) for references). These effects seem to result directly from changes in the net charge of the histone tails upon acetylation rather than from the presence of the actual mark. Besides biophysical experiments, genetic studies, for example, on the acetylation of the histone variant H2A.Z in *Tetrahymena* (Ren et al., "Histone H2A.Z Acetylation Modulates an Essential Charge Patch," *Mol Cell* 7:1329-1335 (2001)) and of the H4 tail in *Saccharomyces cerevisiae* (Megee et al., "Genetic Analysis of Histone H4: Essential Role of Lysines Subject to Reversible Acetylation," *Science* 247:841-845 (1990)), support such a global readout of this modification via direct effects on nucleosome and chromatin structure (see also (Kristjuhan et al., "Transcriptional Inhibition of Genes With Severe Histone h3 Hypoacetylation in the Coding Region," *Mol Cell* 10:925-933 (2002)).

However, other studies have shown that the biological effects of certain distinct marks appear to rely more on specific local binding factors. This docking of effectors to post-translationally modified chromatin is reminiscent of the modular interactions in other signaling pathways (see for example the recruitment of SH2 domains to phospho-tyrosines; for references see (Pawson et al., "Protein-protein Interactions Define Specificity in Signal Transduction," *Genes Dev* 14:1027-1047 (2000)). Bromodomains present in several HATs and chromatin remodeling proteins, as well as in the general transcription factor TAF250, bind acetylated lysines (for review see (Zeng et al., "Bromodomain: an Acetyl-lysine Binding Domain," *FEBS Lett* 513:124-128 (2002)). Sequential recruitment and anchoring of bromodomain-containing factors and complexes to the promoter region is indeed crucial for the activation of some genes (Agalioti et al., "Deciphering the Transcriptional Histone Acetylation Code for a Human Gene," *Cell* 111:381-392 (2002) and Hassan et al., "Function and Selectivity of Bromodomains in Anchoring Chromatin-Modifying Complexes to Promoter Nucleosomes," *Cell* 111:369-379 (2002)). Proteins containing certain chromodomains, on the other hand, have been predicted to have affinity for methylated lysines (Jacobs et al., "Structure of HP1 Chromodomain Bound to a Lysine 9-methylated Histone H3 Tail," *Science* 295:2080-2083 (2002)). In fact, heterochromatin protein 1 (HP1) can bind to methylated H3-K9 (Jacobs et al., "Specificity of the HP1 Chromo Domain for the Methylated N-terminus of Histone H3," *Embo J* 20:5232-5241 (2001); Bannister et al., "Selective Recognition of Methylated Lysine 9 on Histone H3 by the HP1 Chromo Domain CBP/p300 as a Co-factor for the Microphthalmia Transcription Factor," *Nature* 410:120-124 (2001); and Lachner et al., "Methylation of Histone H3 Lysine 9 Creates a Binding Site for HP1 Proteins," *Nature* 410:116-120 (2001)), and more recent work suggests that the silencing protein Polycomb (Pc) can bind methylated H3-K9 and/or methylated H3-K27 (Cao et al., "Role of Histone H3 Lysine 27 Methylation in Polycomb-group Silencing," *Science* 298:1039-1043 (2002); Czermin et al., "*Drosophila* Enhancer of Zeste/ESC Complexes Have a Histone H3 Methyltransferase Activity that Marks Chromosomal Polycomb Sites," *Cell* 111:185-196 (2002); and Kuzmichev et al., "Histone Methyltransferase Activity Associated with a Human Multiprotein Complex Containing the Enhancer of Zeste Protein," *Genes Dev* 16 (2002)). It will be interesting to determine if other chromodomain-containing proteins bind yet other sites of lysine methylation in histones, or potentially, in non-histone proteins. Considering the enormous variability of histone modifications, it is likely that a number of other recognition modules still await discovery.

Already, several short clusters of adjacent or closely-spaced modifiable residues are observed in all core histones and well studied 'hot spots' of clustered marks punctuate the tails of H3 and H4 (FIG. 3). Whereas in vitro experiments using purified enzymes imply that only a limited number of potential combinations of marks on single histones and possibly nucleosomes might exist (Fischle et al., "Histone and Chromatin Cross-talk," *Curr. Opin. Cell Biol.* 15:172-83 (2003)), initial mass spectrometric analysis of histones purified from various cellular sources point to more complex modification patterns in vivo. It seems unlikely that the multiple covalent marks found on histones have evolved independently. The extreme high density and versatility observed might instead serve valuable biological purposes—especially since most sites of post-translational modification are extremely conserved.

The present invention is directed to a novel histone modification biological readout in the form of a binary switch and to uses for that binary switch.

SUMMARY OF THE INVENTION

The present invention relates to a method of modulating a chromatin binding protein or complex which binds to a histone at an amino acid capable of having a functional group. This method involves phosphorylating or dephosphorylating a serine or threonine on the histone proximate to the amino acid under conditions effective to modulate the chromatin binding protein or complex.

Another aspect of the present invention relates to a method of treating or preventing cancer in a subject. This involves phosphorylating or dephosphorylating a serine or threonine on a histone proximate to an amino acid capable of having a functional group under conditions effective to treat or prevent cancer in the subject.

The present invention is also directed to a method of screening therapeutics which treat or prevent cancer in a subject. This involves providing a candidate compound and contacting the candidate compound with a histone comprising a serine or threonine proximate to an amino acid capable of having a functional group. A candidate compound which modulates the protein by phosphorylating or dephosphorylating the serine or threonine is identified as potentially useful in treating or preventing cancer.

The present invention also relates to an antibody or binding portion thereof raised against a binary switch on a histone comprising a phosphorylated serine or threonine proximate to an amino acid bound to a functional group.

A further aspect of the present invention relates to a method of detecting a condition, in a subject, mediated by a binary switch on a histone comprising a phosphorylated serine or threonine proximate to an amino acid bound to a functional group. This involves providing the antibody or binding portion described above and contacting the antibody or binding portion with a sample from the subject. It is then determined whether the antibody or binding portion binds to the sample. This indicates that the subject is positive for the condition.

Several covalent modifications or amino acids, such as acetylation and phosphorylation, are enzymatically reversible. Other modifications, such as lysine methylation, appear to be more stable, perhaps permanent (Bannister et al., "Histone Methylation: Dynamic or Static," *Cell* 109:801-06 (2002), which is hereby incorporated by reference in its entirety). To date, no lysine demethylase has been identified. Nevertheless, proteins have evolved to recognize and bind to lysine-methyl marks. Many of these "effectors" are repressive in function (ie. HP1 and Polycomb), using their chromodomains as the methyl-lysine binding "module" (Fischle et al., "Molecular Basis for the Discrimination of Repressive Methyl-Lysine Marks in Histone H3 by Polycomb and HP1 Chromalomains," *Genes Dev.* 17:1870-81 (2003), which is hereby incorporated by reference in its entirety).

Binary switches provide a molecular mechanism by which all types of methyllysine-binding effectors can be released form chromatin (gene) targets. Understanding the "rules" by which binding effectors can be disengaged from chromatin may provide novel ways to activate genes which are inappropriately silenced in disease states such as cancer. In reverse logic, learning how to inactivate binary switches may facilitate the residence time that the effector (positive or negative) is bound to its target gene. The existence of binary switching mechanisms in other proteins may provide for novel therapeutic intervention strategies designed to perturb these signaling networks that are critically dependent upon these protein recognition steps. Finally, the development of switch antibodies will facilitate the detection of switches in histone and non-histone proteins.

BRIEF DESCRIPTION OF THE DRAWINGS

In FIG. 1A, the potential 'choices' of the modification status of different histone residues. P: phosphorylation of serine or threonine (S/T); Ac: acetylation of lysine (K); mono-, di- and tri-methylation of lysine; mono- or di-methylation (symmetric or asymmetric) of arginine (R); Ub: mono-ubiquitination of lysine; and SUMO: sumolation of lysine (note: sumolation has not been detected on cellular histones). FIG. 1B shows the local cross-talk on the human H3 N-terminal tail domain. The sequence of the N-terminal tail of H3 (aa 1-40; SEQ ID NO: 1) and the four α-helices (represented by boxes) of the globular domain of H3 are shown (human H3; note the position of the highly conserved cysteine 110, C110). Sites of known modifications are listed [(M): (mono-, di-, tri-) methylation]. K9 and K14 have been found to be methylated or acetylated (box). ARKS repeats that contain two sites of methylation (K9 and K27) as well as known sites of phosphorylation (S10 and S28) are highlighted. Primary modifications that positively ('go' or permissive) or negatively ('stop' or repressive) influence the modification of other sites in in vitro enzymatic assays are listed on the left. The situation is likely to be more complicated in vivo, and enzymes that modify the same site might be influenced differently by the modification-state of their substrate. For example, although methylation on K4 impairs the ability of Su(var)3-9 to methylate K9, and methylation on K9 inhibits the enzymatic activity of SET7/9 to methylate K4 (Wang et al., "Purification and Functional Characterization of a Histone H3-lysine 4—Specific Methyltransferase," *Mol Cell* 8:1207-1217 (2001), which is hereby incorporated by reference in its entirety), the *Drosophila* HMT, Ash1, seems to be able to methylate both K4 and K9 at the same time (Beisel et al., "Histone Methylation by the *Drosophila* Epigenetic Transcriptional Regulator Ash1," *Nature* 419:857-862 (2002), which is hereby incorporated by reference in its entirety). FIG. 1C shows the local cross-talk on the human H4 N-terminal tail domain. The sequence of the N-terminal tail of H4 (aa 1-26; SEQ ID NO: 2) and the three α-helices (represented by boxes) of the globular domain of H4 are shown (human sequence). Interference and 'communication' between known modifications are outlined as in FIG. 1B. The extreme amino-terminal residues, SGRGK (boxed), are known to be modified by phosphorylation (S1), methylation (R3), and acetylation (K5) in some species. As such, these residues might form a 'modification cassette' that remains poorly understood. The patch of basic residues (KRHRK) can be acetylated (K16) or methylated (K20), which represents a mutually exclusive pair of modifications that either facilitate or repress gene expression (Nishioka et al., "PR-Set7 is a Nucleosome-specific Methyltransferase that Modifies Lysine 20 of Histone H4 and is Associated with Silent Chromatin," *Mol Cell* 9:1201-1213 (2002), which is hereby incorporated by reference in its entirety). For both, H3 (FIG. 1B) and H4 (FIG. 1C), short sequence patches in the globular domains that were shown to play an important role in gene silencing in budding yeast are underlined (Park et al., "A Core Nucleosome Surface Crucial for Transcriptional Silencing," *Nat Genet* 32:273-279 (2002), which is hereby incorporated by reference in its entirety).

FIG. 2A is a schematic representation of four core histones [one copy of each of H2A, H2B, H3, and H4] as seen in the context of a nucleosome (residues are numbered according to the sequences of human histones). The dashed line represents the unstructured tails. Monoubiquitination of the H2A and the H2B C-terminal tails (K119 in H2A and K120 in H2B) is shown. In budding yeast, only H2B is known to be ubiquitinated (H2B-K120 of the human sequence corresponds to H2B-K123 in this organism). In a 'trans-tail' pathway, this modification is necessary for methylation of H3 on K4 and K79 (arrows), but not K36 (see text for details). A conserved cysteine in H3 (C110) is indicated (dot). As shown in FIG. 2B, in an array of nucleosomes, different modifications on separate histones (X or Y) might influence each other in a positive or negative way. For example, it has been postulated that methylation of H3 on K9 could be spread over larger domains by recruitment of an HP1-Su(var)3-9 complex to sites of H3-K9 methylation (positive 'communication' X<=>X) (Nakayama et al., "Role of Histone H3 Lysine 9 Methylation in Epigenetic Control of Heterochromatin Assembly," *Science* 292:110-113 (2001) and Bannister et al., "Selective Recognition of Methylated Lysine 9 on Histone H3 by the HP1 Chromo Domain CBP/p300 as a Co-factor for the Microphthalmia Transcription Factor," *Nature* 410:120-124 (2001), which are hereby incorporated by reference in their entirety). Similarly, boundaries for modification spreading could be established by inhibition/exclusion of different modifications (negative 'communication' X>=<Y). On another level, a single modification could regulate the modification pattern of a larger region of nucleosomes ('master control switch', Z). Ubiquitination of H2B in budding yeast could be such a 'master control switch' because of its relatively low abundance in comparison to the methylation on H3-K4 and H3-K79, which are both dependent on this modification (see text). Since histone ubiquitination might be less stable than histone methylation, it is also possible that ubiquitin is removed after a methylation event on the same nucleosome. FIG. 2C shows chromatin cross-talk may be mediated and read by different mechanisms. Effector modules and histone-modifying complexes could be recruited by certain marks but excluded/repelled by other modifications. Effectors or effector complexes that contain more than one recognition module for a certain modification (or modification pattern) could mediate long-range effects. Such binding factors could serve as 'bridging clamps' to bring together and potentially anchor distant nucleosomal arrays. In addition, modifying enzymes that contain binding modules or bind to effectors could reinforce and expand the modification pattern to adjacent nucleosomes (chromatin/histone modifiers).

FIGS. 6A-D show the putative 'cassettes' and 'switches' in histone and non-histone proteins. FIG. 6A shows the conservation (and divergence) of a putative 'modification cassette' motif in the extreme N-terminus of H4 (Hs H4 (SEQ ID NO: 5) and Tet H4 (SEQ ID NO: 8)) and H2A.1 (SEQ ID NO: 6) as well as in H2A.Z (SEQ ID NO: 7), a minor histone variant. Note the change of Ala1 for Ser1 concomitant with the loss of Arg3 exhibited by some H4 and H2A species. FIG. 6B shows the potential p53 'modification cassettes' and 'switches' (SEQ ID NO: 9). Post-translational modifications in the C-terminal basic domain of human p53 are denoted. Putative 'modification cassettes' are indicated by boxes. FIGS. 6C-D show sequence comparison of putative 'modification cassettes' motifs in histones and other proteins. FIG. 6C shows sequence comparison of putative 'modification cassettes' motifs in Hs H4 (SEQ ID NO: 10); Hs AML1/RUNX1 (SEQ ID NO: 11); Hs AML2/RUNX3 (SEQ ID NO: 11); Hs AML3/RUNX2 (SEQ ID NO: 11); and Dm RUNT (SEQ ID NO: 12). FIG. 6D shows sequence comparison of putative 'modification cassettes' motifs in Dm H4 (SEQ ID NO: 13); Dm Polycomb (SEQ ID NO: 14); Hs NRF1 (SEQ ID NO: 15); and Hs MCM4 (SEQ ID NO: 16). The [SGRGK] and [TGRGK] sequence stretches of human (SEQ ID NO: 10) and *Drosophila* (SEQ ID NO: 13) H4, respectively, were analyzed against the Swiss-Prot database (Release 41.11) using the Pattern Search algorithm. Note that the indicated cassettes are evolutionarily very conserved in the AML/RUNX protein family as well as in the NRF1 and MCM4 proteins.

FIGS. 7A-B show the dual modification of the histone H3 tail by methylation on Lys 9 and phosphorylation on Ser 10 (FIG. 7A shows SEQ ID NO: 17; FIG. 7B shows SEQ ID NO: 18).

FIGS. 8A-C show immunological analyses using the rabbit polyclonal antibodies raised against a synthetic peptide corresponding to the H3 tail tri-methylated at Lys 9 and phosphorylated at Ser 10 (me3K9pS10).

FIG. 11A shows the alignment of different chromodomains with affinity for histone methyl marks (dmPc (SEQ ID NO:

19); dmHP1 (SEQ ID NO: 20); mCBX2 (Pc1, PcM33) (SEQ ID NO: 21); hCBX4 (Pc2) (SEQ ID NO: 22); hCBX6 (Pc3) (SEQ ID NO: 23); hCBX7 (SEQ ID NO: 24); hCBX8 (SEQ ID NO: 25); hHP1α (SEQ ID NO: 26); hHP1β (SEQ ID NO: 27); hHP1γ (SEQ ID NO: 28); hCDY (SEQ ID NO: 29); hSuv39h1 (SEQ ID NO: 30); and hSuv39h2 (SEQ ID NO: 31)). A conserved Glu residue predicted to make contact to the H3 tail exiting the chomodomain binding groove is highlighted.

Figure 12:
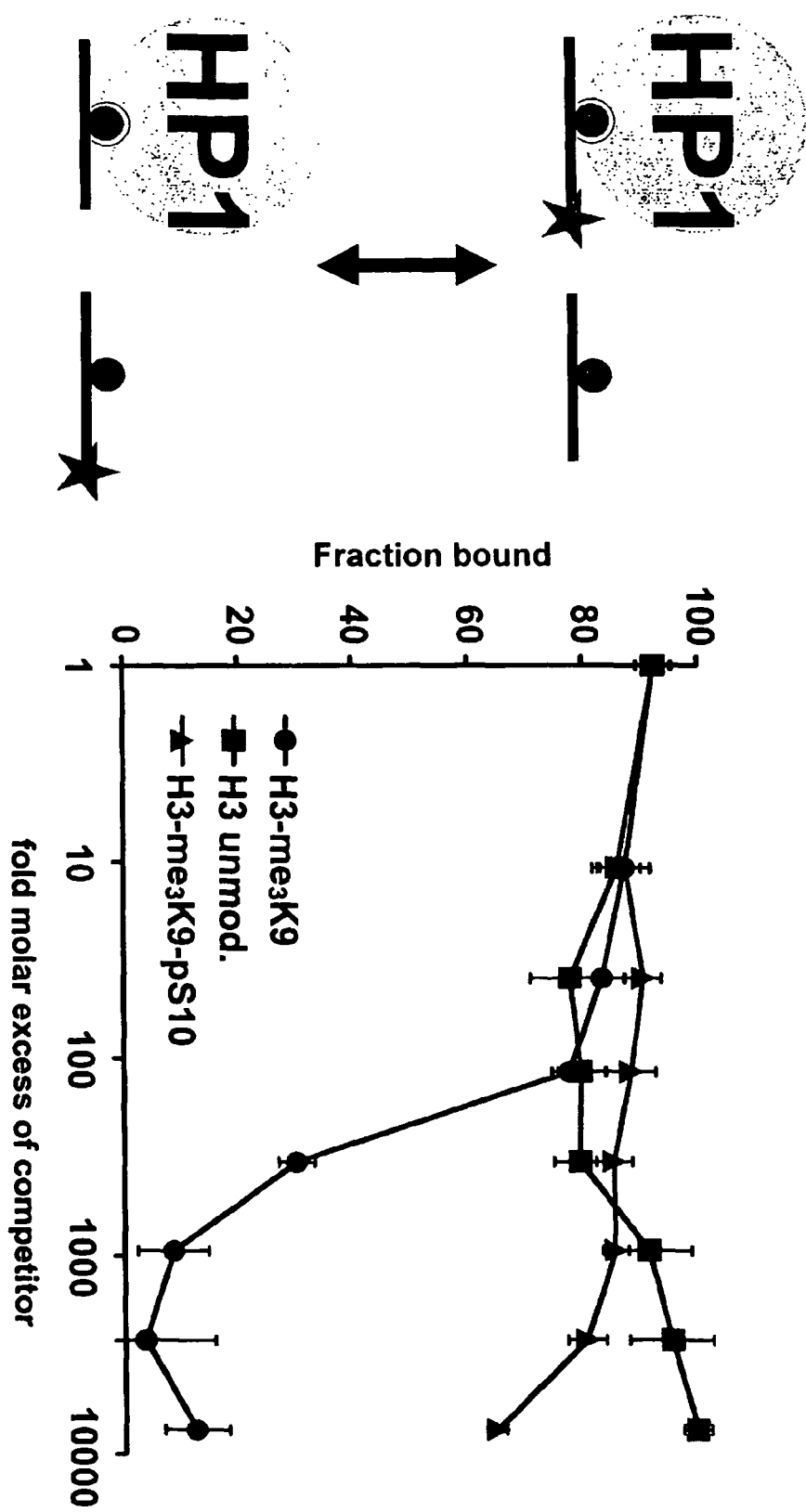

FIG. 12 shows the binding of HP1 to the methylated H3 tail is reversible.

Figure 13A:
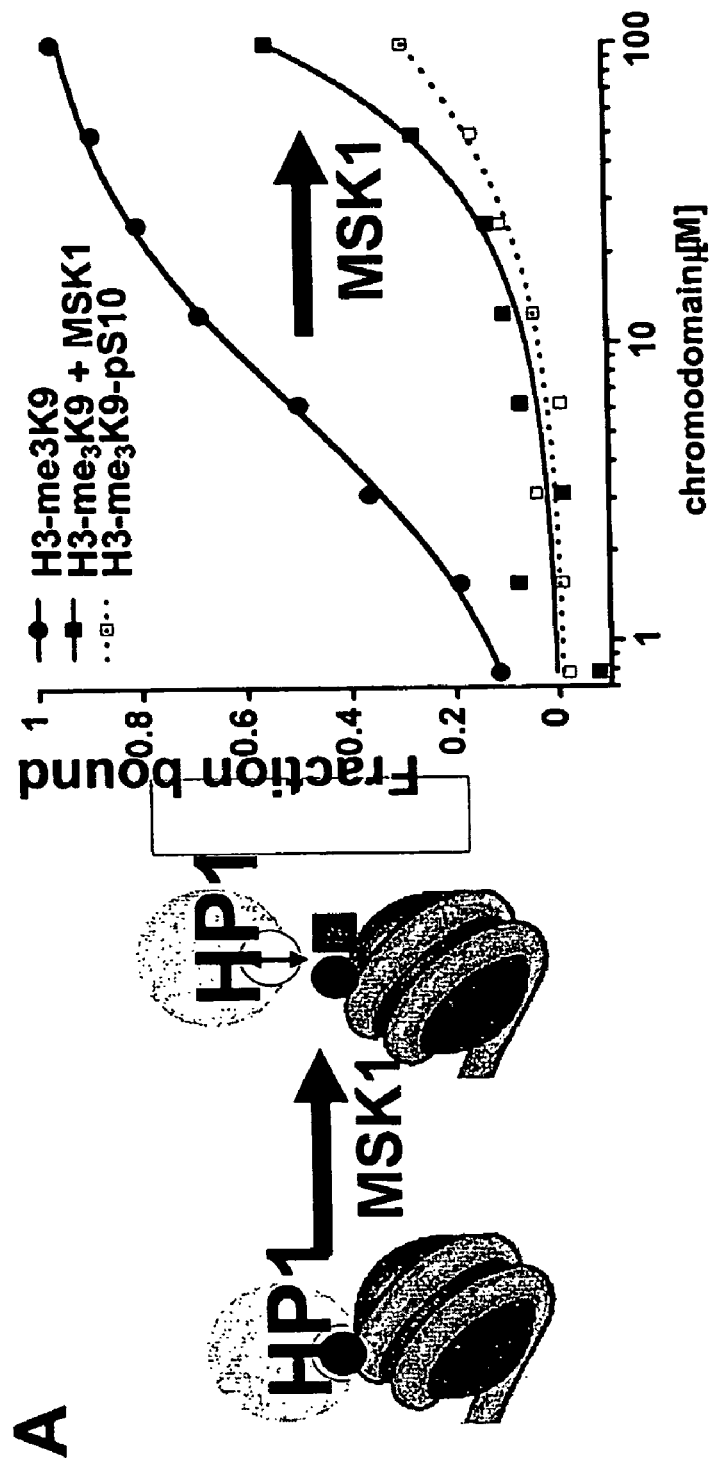
Figure 13:
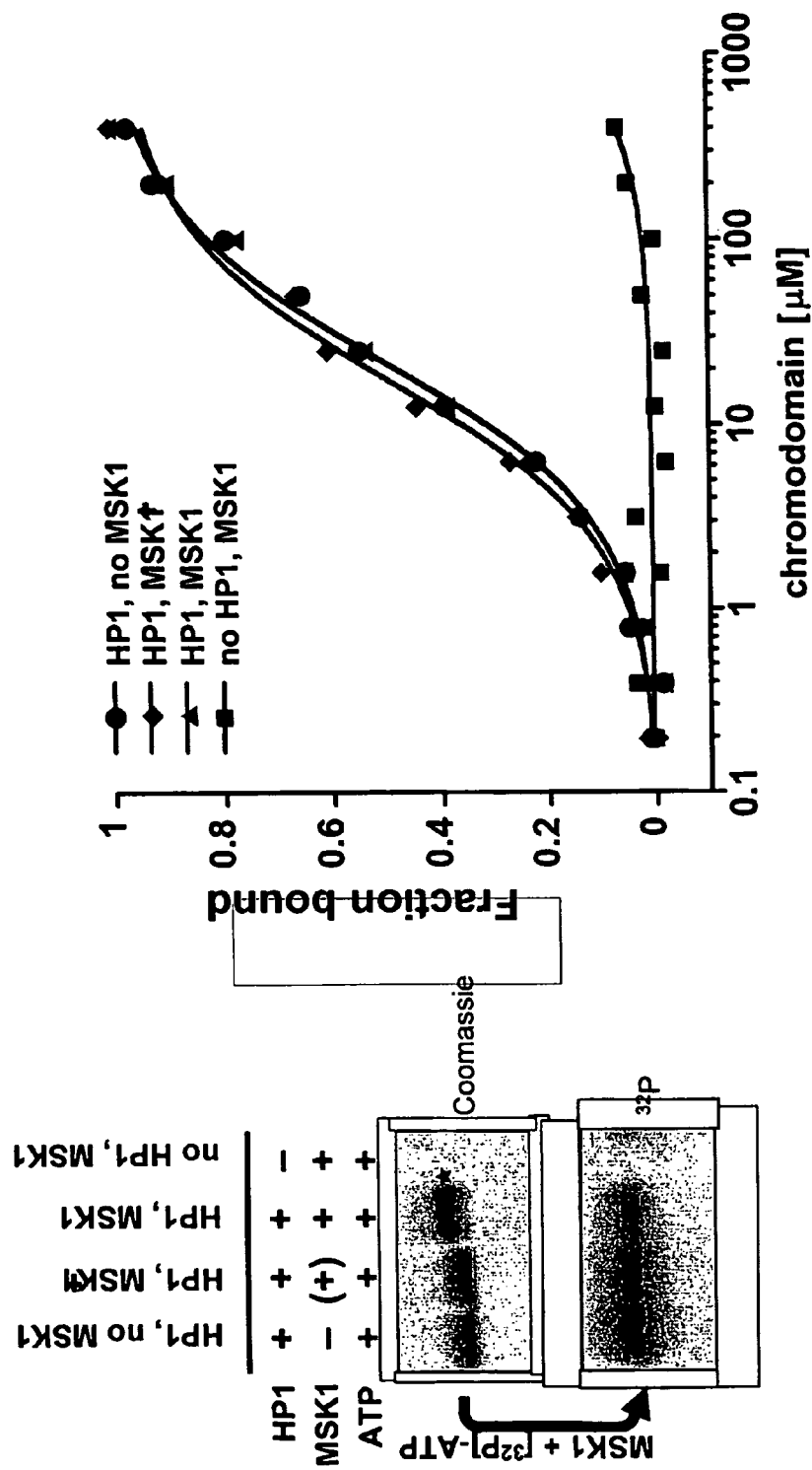

FIGS. 13A-D shows the phosphorylation of Ser 10 leads to dissociation of HP1 from the H3 tail methylated on Lys 9. As shown in FIG. 13D, the phosphorylation of the 10×HIS-HP1 polypeptide occurs in the linker region. The indicated recombinant 6×HIS (SEQ ID NO: 32) and 10×HIS (SEQ ID NO: 33) HP1 polypeptides were incubated with MSK1 and [32P]-ATP (1 Hr, 30° C.).

FIGS. 14A-D shows the real time kinetic analysis of switching.

DETAILED DESCRIPTION OF THE INVENTION

The present invention relates to a method of modulating a chromatin binding protein or complex which binds to a histone of an amino acid capable of having a functional group. This method involves phosphorylating or dephosphorylating a serine or threonine on the histone proximate to the amino acid under conditions effective to modulate the chromatin binding protein or complex.

When the serine or threonine on the histone is phosphorylated, the chromatin binding protein or complex is removed. On the other hand, when the serine or thronine on the histone is dephosphorylated, the chromatin binding protein or complex is bound. The serine or threonine is desirably adjacent or at least near the amino acid. In a particularly preferred embodiment, the amino acid is lysine and the functional group is methyl. Other suitable amino acids are arginine or any other amino acid capable of being modified covalently. The functional group can alternatively be a acetyl, ubiquitin, or sumolyl group. A chromatin binding protein or complex which binds to a non-histone protein can also be modulated in accordance with the present invention.

Another aspect of the present invention relates to a method of treating or preventing cancer in a subject. This involves phosphorylating or dephosphorylating a serine or threonine on a histone proximate to an amino acid capable of having a functional group under conditions effective to treat or prevent cancer in the subject.

In accordance with this aspect of the present invention, the cancer is selected from the group consisting of breast cancer, colon cancer, prostate cancer, lung cancer, and skin cancer.

The protein can be a tumor suppressor gene inhibitor or an oncogenic protein. Two of the best-studied "modification cassettes" are [STGR*GK] in H4 and ARK*S/T in H3 (Fischle et al., "Binary Switches and Modification Cassettes in Histone Biology and Beyond," Nature 425:475-79 (2003), which is hereby incorporated by reference in its entirety). Interestingly, both of the asterisk marked residues (R* and K*) are known to be methylated in nonhistone proteins with potential cancer (cell purification) relevancy. Acute myeloid leukemia protein 1 (AML1) and a well-known histone methyltransferase (G9a) have one of the above two cassettes. Thus, phosphorylation at the S/T residue may serves as a "binary switch" to govern the binding/release of interacting proteins that modulate the function of these proteins. While the well-known tumor suppressor protein p53 does not have these motifs, its C-terminus is heavily modified by phosphorylation, acetylation and methylation. Thus, binary switching may govern critical interaction of p53 function and a wide range of yet unknown histone and nonhistone proteins.

The present invention is also directed to a method of screening therapeutics which treat or prevent cancer in a subject. This involves providing a candidate compound and contacting the candidate compound with a histone comprising a serine or threonine proximate to an amino acid, capable of having a functional group. A candidate compound which modulates the protein by phosphorylating or dephosphorylating the serine or threonine is identified as potentially useful in treating or preventing cancer. This method can be carried out with a variety of formats, including the chromatin immunoprecipitation assay (Ren, et. al., "Use of Chromatin Immunoprecipitation Assays in Genome-Wide Location Analysis of Mammalian Transcript Factors" (Chapter 20); Oberly, et. al., "High Throughput Screening of Chromatin Immunoprecipitates Using CpG-Island Microarrays" (Chapter 21); Ciccone, et. al., "Chromatin Immunoprecipitation in the Analysis of Large Chromatin Domains Across Murine Antigen Receptor Loci" (Chapter 22); and Bernstein, et. al., "The Use of Chromatin Immunoprecipitation Assays in Genome-Wide Analyses of Histone Modifications" (Chapter 23), all in *Methods in Enzymology*, Volume 376 edited by David Allis, Carl Wu (2004), which are hereby incorporated by reference in their entirety).

The present invention also relates to an antibody or binding portion thereof raised against a binary switch on a histone comprising a phosphorylated serine or threonine proximate to an amino acid bound to a functional group.

Antibodies of the present invention may be either monoclonal antibodies or polyclonal antibodies.

Monoclonal antibody production may be carried out by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler et al., *Nature* 256:495 (1975), which is hereby incorporated by reference in its entirety.

Mammalian lymphocytes are immunized by in vivo immunization of the animal (e.g., a mouse) with the binary switch antigen. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (Milstein et al., *Eur. J. Immunol.* 6:511 (1976), which is hereby incorporated by reference in its entirety). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the binary switch antigen subcutaneously to New Zealand white rabbits which have first been bled to obtain pre-immune serum. The antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentobarbital 150 mg/Kg IV. This and other procedures for raising polyclonal antibodies are disclosed in Harlow et. al., editors, *Antibodies: A Laboratory Manual* (1988), which is hereby incorporated by reference in its entirety.

Antibodies that are essentially human may be produced in transgenic mammals, especially transgenic mice that are genetically modified to express human antibodies. Methods for making chimeric and humanized antibodies are also known in the art. For example, methods for making chimeric antibodies include those described in U.S. Pat. Nos. 4,816,397 and 4,816,567, which are hereby incorporated by reference in their entirety. Methods for making humanized antibodies are described in U.S. Pat. No. 5,225,539, which is hereby incorporated by reference in its entirety.

The preferred method for humanization of antibodies is called CDR-grafting. In CDR-grafting, the regions of the mouse antibody that are directly involved in binding to antigen, the complementarity determining region of CDRs, are grafted into human variable regions to create "reshaped human" variable regions. These fully humanized variable regions are then joined to human constant regions to create complete "fully humanized" antibodies.

In order to create fully humanized antibodies that bind well to an antigen, it is advantageous to design the reshaped human variable regions carefully. The human variable regions into which the CDRs will be grafted should be carefully selected, and it is usually necessary to make a few amino acid changes to critical positions within the framework regions (FRs) of the human variable regions.

For example, the reshaped human variable regions may include up to ten amino acid changes in the FRs of the selected human light chain variable region, and as many as twelve amino acid changes in the FRs of the selected human heavy chain variable region. The DNA sequences coding for these reshaped human heavy and light chain variable region genes are joined to DNA sequences coding for the human heavy and light chain constant region genes, preferably γ1 and κ, respectively. The reshaped humanized antibody is then expressed in mammalian cells and its affinity for its target compared with that of the corresponding murine antibody and chimeric antibody.

Methods for selecting the residues of the humanized antibody to be substituted and for making the substitutions are well known in the art. See, for example, Co et al., *Nature* 351:501-502 (1992); Queen et al., *Proc. Natl. Acad. Sci. USA* 86:10029-1003 (1989); and Rodrigues et al., *Int. J. Cancer*, Supplement 7:45-50 (1992), which are hereby incorporated by reference in their entirety. A method for humanizing and reshaping the 225 anti-EGFR monoclonal antibody is described by WO 96/40210, which is hereby incorporated by reference in its entirety. This method can be adapted to humanizing and reshaping antibodies against other proteins.

Methods for making single chain antibodies are also known in the art. Some examples include those described by European Patent Application No. 502 812 and Wels et al., *Int. J. Cancer* 60:137-144 (1995), which are hereby incorporated by reference in their entirety. Single chain antibodies may also be prepared by screening phage display libraries.

A further aspect of the present invention relates to a method of detecting a condition, in a subject, mediated by a binary switch on a histone comprising a phosphorylated serine or threonine proximate to an amino acid bound to a functional group. This involves providing the antibody or binding portion described above and contacting the antibody or binding portion with a sample from the subject. It is then determined whether the antibody or binding portion binds to the sample. This indicates that the subject is positive for the condition.

This method is particularly useful is detecting cancer, including any of the above-mentioned cancers.

This method can be carried out in vivo or in vitro.

The in vivo aspect of this invention can be carried out by administering labeled antibodies or binding portions thereof to a subject and scanning or imaging the subject for binding events by such labeled entities.

The in vitro form of this method can be used in conjuction with urine, blood, biopsy, and tumor samples taken from the subject.

Figure 4:
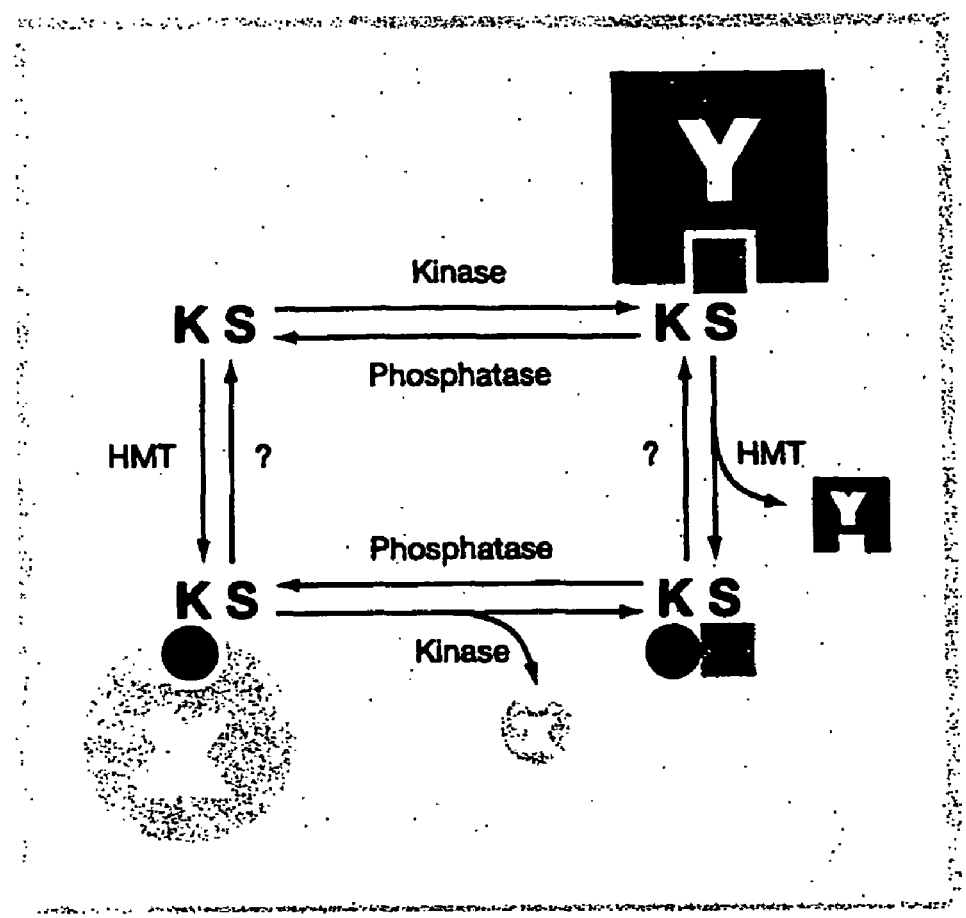
FIG. 4 shows local binary switches in accordance with the present invention. Post-translational modification of certain amino acids (i.e. methylation of lysines [K] or/and phosphorylation of serines [S]) in the core histones results in recruitment of effector proteins (X, Y). Additional covalent modification of the site adjacent to a previously set covalent mark that has engaged an effector module leads to consecutive loss of binding to that factor. The general concept here for 'methyl/phos switches' could be applicable to other combinations of marks (for example, 'acetyl/phos', 'ubiquityl/phos', etc.). Question marks refer to the yet unknown existence of histone lysine demethylases. HMT, histone methyltransferase.

Differential readout of distinct combinations of marks could, for example, be achieved by 'local switching' mechanisms, such as the 'methyl/phos switch' shown in FIG. 4. In this binary switch, phosphorylation of a site adjacent to (or nearby) a methyl-mark that engages an effector module could lead to consecutive loss of binding to that factor. The observed weak interaction of chromatin modules with their cognate marks could generally allow for rapid 'on-off' binding, which is then further regulated by modification of another neighboring site in the 'off'-state ($K_D \sim 10^{-4}$-$10^{-6}$ M for both, chromodomain/methyl-lysine and bromodomain/acetyl-lysine interactions). Such a kinetically-controlled binding mechanism of effector modules is sustained by the recent demonstration that binding proteins of heterochromatic methyl-marks have a fast exchange rate with their environment and are not statically bound to their target sites (Festenstein et al., "Modulation of Heterochromatin Protein 1 Dynamics in Primary Mammalian Cells," *Science* 299:719-21 (2003) and Cheutin et al., "Maintenance of Stable Heterochromatin Domains by Dynamic HP1 Binding," *Science* 299:721-5 (2003), which are hereby incorporated by reference in their entirety).

In particular, 'binary switches' could add an important dynamic nature to the readout of marks that themselves have very low turnover rates. For example, it is currently not understood if and how methyl-marks in histones are reversed, and histone-demethylating enzymes are unknown (Bannister et al., "Histone Methylation: Dynamic or Static?," *Cell* 109:801-6 (2002), which is hereby incorporated by reference in its entirety). Some histone methyl-lysine marks appear to be stably maintained over several cell generations (Ayyanathan et al., "Regulated Recruitment of HP1 to a Euchromatic Gene Induces Mitotically Heritable, Epigenetic Gene Silencing: A Mammalian Cell Culture Model of Gene Variegation," *Genes Dev.* 17:1855-69 (2003), which is hereby incorporated by reference in its entirety); yet, it is conceivable and likely that proteins bound to methyl-marks are removed at some point in the cell cycle or during development of a complex organism. Therefore, 'methyl/phos switching' could be a widespread mechanism regulating the binding and release of effector modules to more stable methyl-marks. Nevertheless, similar switches could also be operational for more labile marks (i.e. 'acetyl/phos' or 'ubiquitin/phos' switches). In addition, the binding of yet to be discovered phopho-binding effector modules ('Y' in FIG. 4) could be regulated by nearby or adjacent 'off' switches.

One site where a binary 'methyl/phos switch' is operational is the Lys9/Ser10 region of H3. Methylation of Lys9 by SET-type histone methyltransferases (HMT) like Su(var)3-9 and G9a has been well documented and is associated with the establishment and maintenance of heterochromatic domains in many organisms (Lachner et al., "The Many Faces of Histone Lysine Methylation," *Curr. Opin. Cell Biol.* 14:286-98 (2002), which is hereby incorporated by reference in its entirety). The chromodomain of HP1 binds specifically to this mark and local HP1 recruitment is sufficient for mediating heterochromatin formation (Li et al., "Effects of Tethering HP1 to Euchromatic Regions of the *Drosophila* Genome," *Development* 130:1817-24 (2003), which is hereby incorporated by reference in its entirety) and accompanies gene silencing (Ayyanathan et al., "Regulated Recruitment of HP1 to a Euchromatic Gene Induces Mitotically Heritable, Epigenetic Gene Silencing: A Mammalian Cell Culture Model of Gene Variegation," *Genes Dev.* 17:1855-69 (2003), which is hereby incorporated by reference in its entirety). Genome-wide mitotic phosphorylation of H3 Ser10 is catalyzed by aurora B-type kinases, and several other enzymes mediate a more localized and targeted employment of phospho-Ser10 in response to immediate-early gene signalling (Cheung et al., "Signaling to Chromatin Through Histone Modifications," *Cell* 103:263-71 (2000) and Berger, "Histone Modifications in Transcriptional Regulation," *Curr. Opin. Gen. Dev.* 12:142-8 (2002), which are hereby incorporated by reference in their entirety). Whereas initial reports using enzymatic in vitro assays pointed to a mutually exclusive existence of the methyl-Lys9 and phospho-Ser10 marks (Rea et al., "Regulation of Chromatin Structure by Site-specific Histone H3 Methyltransferases," *Nature* 406:593-9 (2000), which is hereby incorporated by reference in its entirety), analysis of the in vivo modification pattern of H3 isolated from HeLa cells points to the coexistence of both marks on the same histone tail—especially during mitosis.

Structural examination of the chromodomain of HP1 bound to the H3 tail methylated on Lys9 (Jacobs et al., "Structure of HP1 Chromodomain Bound to a Lysine 9-methylated Histone H3 Tail," *Science* 295:2080-3 (2002) and Nielsen et al., "Structure of the HP1 Chromodomain Bound to Histone H3 Methylated at Lysine 9," *Nature* 416:103-7 (2002), which are hereby incorporated by reference in their entirety), allows the prediction that additional phosphorylation of Ser10 could severely diminish the binding affinity of HP1 to its cognate mark (i.e. release of 'X' in FIG. 4). Indeed, in in vitro assays chromodomains show almost complete loss of binding to dual modified peptides containing the methyl-Lys9 and phospho-Ser10 marks. In accordance with FIG. 4, mitosis (or meiosis) or pathways of gene activation can drive the phosphorylation of the proposed 'methyl/phos' switch allowing for the release, and potential clearing, of 'negative' chromatin effectors like HP1 that repress transcription. This sequence of events could consecutively permit the docking of positive effectors that drive transcription (e.g. HAT-containing complexes). In support, HP1 is partially liberated from interphase heterochromatin domains as cells enter mitosis (Kellum et al., "Heterochromatin Protein 1 Distribution During Development and During the Cell Cycle in *Drosophila* Embryos," *J. Cell Sci.* 108(4):1407-18 (1995) and Minc et al., "Localization and Phosphorylation of HP1 Proteins During the Cell Cycle in Mammalian Cells," *Chromosoma* 108:220-34 (1999), which are hereby incorporated by reference in their entirety), a cell cycle stage marked by a rapid, transient burst of H3 Ser10 phosphorylation (Cheung et al., "Signaling to Chromatin Through Histone Modifications," *Cell* 103:263-71 (2000), which is hereby incorporated by reference in its entirety). Furthermore, HP1 displays an increased mobility in T-cells after receptor-driven kinase signaling is activated, an observation that is paralleled by a decrease of the immobile fraction of the protein (Festenstein et al., "Modulation of Heterochromatin Protein 1 Dynamics in Primary Mammalian Cells," *Science* 299:719-21 (2003), which is hereby incorporated by reference in its entirety).

Additional support for a Lys9/Ser10 'methyl/phos switch' is derived from the finding that type 1 protein phosphatase (PP1) acts as a mitotic phosphatase targeting phospho-Ser10 as cells exit mitosis (Hsu et al., "Mitotic Phosphorylation of Histone H3 is Governed by Ipl1/aurora Kinase and Glc7/PP1 Phosphatase in Budding Yeast and Nematodes," *Cell* 102:279-91 (2000), which is hereby incorporated by reference in its entirety). PP1 has independently been identified in genetic screens in *Drosophila* as Su(var)3-6 (Reuter et al., "Position Effect Variegation and Chromatin Proteins," *Bioessays* 14:605-12 (1992), which is hereby incorporated by reference in its entirety). Genes of the Su(var) family facilitate heterochromatic gene silencing as assayed by suppression of position effect variegation by mechanisms that have remained elusive for a long time. The 'methyl/phos switches' makes a clear and testable prediction regarding the role of Su(var)3-6 in the above silencing pathway: one role, if not the major role, of PP1 is to remove mitotic phosphates at Ser10 in H3, therefore allowing increased binding of HP1 (genetically identified as Su(var)2-5) to H3 methyl-Lys9 marks, which are themselves added by a H3 Lys9 methyltransferase (Su(var) 3-9).

Other methyl-mark-specific modules will be identified whose binding might be sensitive to neighboring phospho-marks. The best-studied methyl-marks in the H3 tail (Lys4, Lys9 and Lys27), for example, are all adjacent to novel (Thr3) or previously described (Ser10 and Ser28) phospho-acceptors. Whereas the chromodomain of Polycomb preferentially binds the Lys27 methyl-mark (Fischle et al., "Molecular Basis for the Discrimination of Repressive Methyl-Lysine Marks in Histone H3 by Polycomb and HP1 Chromo-domains," *Genes Dev.* 17:1870-81 (2003), which is hereby incorporated by reference in its entirety), a module that 'reads' the H3 Lys4 methyl-mark, which has been associated with an 'on' or 'competent' transcriptional state, has yet to be identified. If such a module exists, its binding to the H3 tail could be regulated by phosphorylation of Thr3. Lys23 in the H3 tail is another methylation site (Waterborg, "Sequence Analysis of Acetylation and Methylation in Two Histone H3 Variants of Alfalfa," *J. Biol. Chem.* 265:17157-61 (1990), which is hereby incorporated by reference in its entirety), and phosphorylation of Thr22 could regulate the biology of this mark. As a result, up to four 'methyl/phos switches' might be operating on the H3 tail alone (FIGS. 3 and 5).

Figure 5:
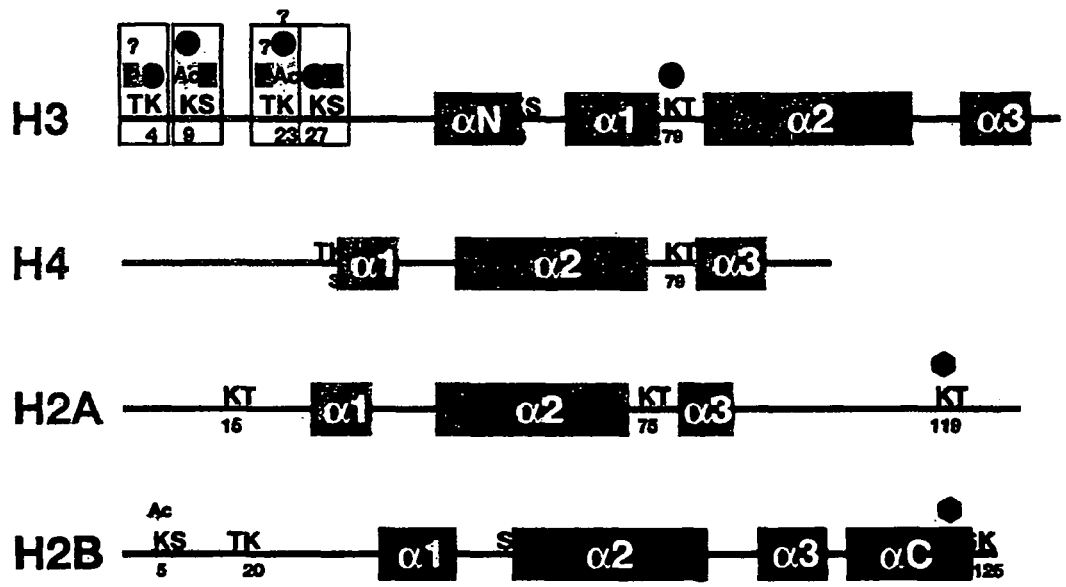
FIG. 5 shows the surveillance of putative 'methyl/phos switches' in core histones. The sequences of all four human core histones were searched for the presence of T/SK and KS/T motifs (T, threonine; S, serine; K, lysine). Known post-translational modifications of such sites are indicated. Boxes frame four likely 'methyl/phos switches' in the H3 tail.

When considering all four core histones, the number and placement of putative binary switches, inside and outside of histone tails, is provocative (FIG. 5). Lys79 of H3, for example, represents the first known methylation site in the histone fold regions (Lachner et al., "An Epigenetic Road Map for Histone Lysine Methylation," *J. Cell Sci.* 116:2117-24 (2003), which is hereby incorporated by reference in its entirety). Remarkably, it also lies adjacent to a potential phosphorylation site, Thr80, and recent genetic screens have implied Lys79Thr80 in a genomic 'silencing cluster' (Park et al., "A Core Nucleosome Surface Crucial for Transcriptional Silencing," *Nature Genet.* 32:273-9 (2002) and Thompson et al., "Identification of a Functional Domain Within the Essential Core of Histone H3 That Is Required for Telomeric and HM Silencing in *Saccharomyces cerevisiae*," *Genetics* 163 (1):447-52 (2003), which are hereby incorporated by reference in their entirety). Interestingly, this cluster involves a corresponding region of H4, Lys79 and Thr80, suggesting that 'methyl/phos switches' might regulate the critical interface between H3 and H4 (note: it is unknown if Lys79 of H4 is methylated or/and if Thr80 of H4 is phosphorylated). The idea that a 'methyl/phos switch' may operate on a critical interface of the H3:H4 dimer is attractive given the importance of this boundary for nucleosome structure and gene regulation (Park et al., "A Core Nucleosome Surface Crucial for Transcriptional Silencing," *Nature Genet.* 32:273-9 (2002), which is hereby incorporated by reference in its entirety).

The exercise of identifying all LysSer/Thr or Ser/ThrLys pairs in all major core histones reveals other remarkable surprises (FIG. 5). All 'switches' are located either in the exposed histone tails, at the edges of helical stretches, or in the connecting loops of the histone fold domains. These sites could, therefore, all be accessible to post-translational modification and function as potential 'switches'. Interestingly, the well-known ubiquitination sites (Lys119 and Lys120 in human H2A and H2B, respectively) are also adjacent to threonine residues, suggesting that switching mechanisms might influence ubiquitin attachment or removal, and/or the readout of ubiquityl-marks (note: it is unknown if Thr120 in H2A or Thr119 in H2B are phospho-acceptors).

Figure 1:
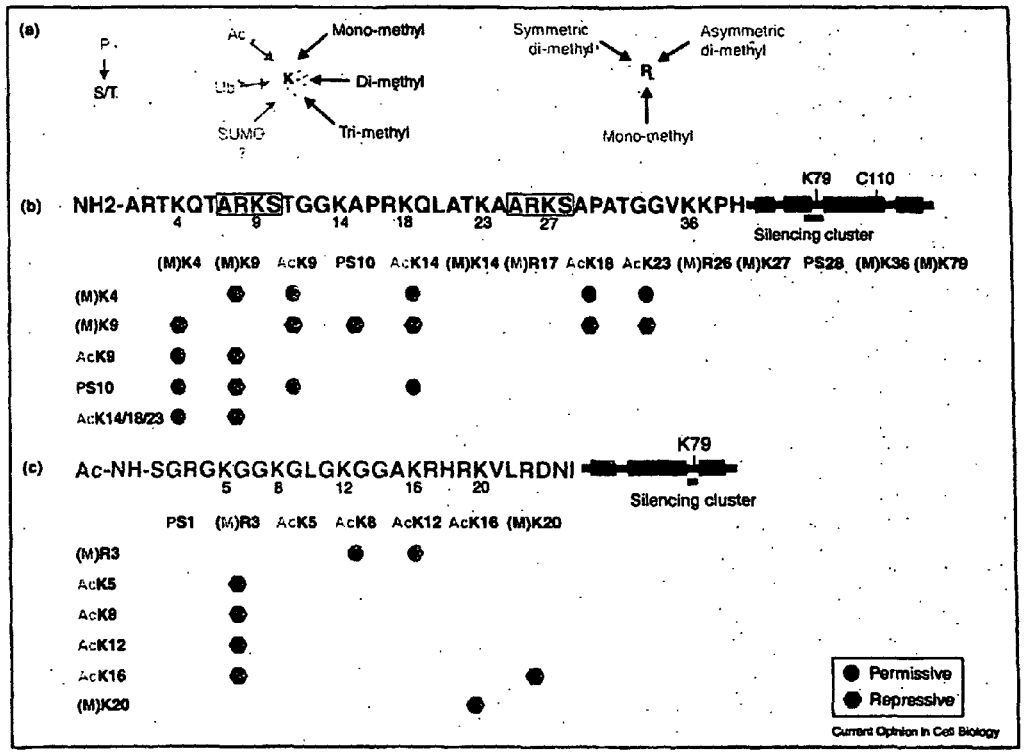
FIGS. 1A-C show the cross-talk at the level of a single histone tail.
Figure 2:
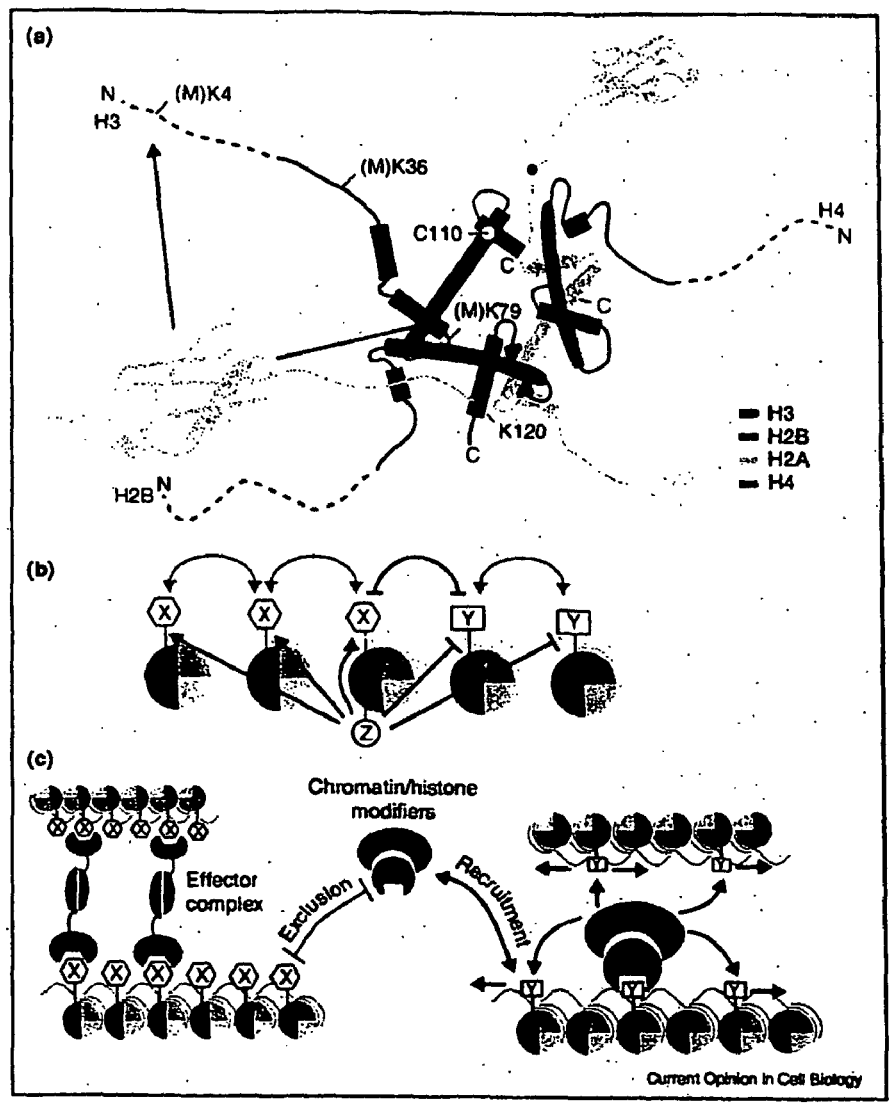
FIGS. 2A-C show the cross-talk at the level of individual nucleosomes and nucleosomal domains.
Figure 3:
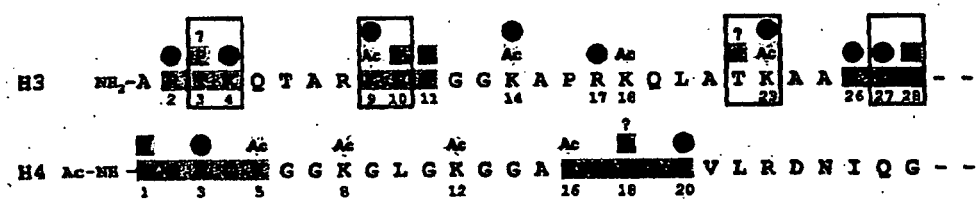
FIG. 3 shows the dense clustering of histone marks. Histone modifications clustered in the N-terminal tails of H3 and H4. The sequences of the first 28 residues of human H3 (SEQ ID NO: 3) and H4 (SEQ ID NO: 4) are denoted, and sites of post-translational modifications are indicated. Note that lysine residues can be mono-, di-, and tri-methylated and arginine residues can be mono-, and di-methylated (symmetric or asymmetric) (Fischle et al., "Histone and Chromatin Cross-talk," *Curr. Opin. Cell Biol.* 15:172-83 (2003), which is hereby incorporated by reference in its entirety). For clarity reasons, these different methylation events are collectively represented as methyl-marks. However, it is now clear that the additional complexity realized in different methylation levels is of great biological significance (Santos-Rosa et al.," Active Genes are Tri-methylated at K4 of Histone H3," *Nature* 419: 407-11 (2002), which is hereby incorporated by reference in its entirety). Question marks accompany modifications that have been less well documented. Methylation of Lys23 has previously been reported in Alfalfa (Waterborg, "Sequence Analysis of Acetylation and Methylation in Two Histone H3 Variants of Alfalfa," *J. Biol. Chem.* 265:17157-61 (1990), which is hereby incorporated by reference in its entirety) and was verified by mass spectrometric analysis using H3 isolated from HeLa cells. Similarly, Thr3 and Thr22 have recently been identified as novel phospho-acceptors in the H3 tail. Older literature provides clues that His18 might be an acid-labile phosphorylation site in H4 (Fujitaki et al., "Characterization of Chemical and Enzymatic Acid-labile Phosphorylation of Histone H4 Using Phosphorus-31 Nuclear Magnetic Resonance," *Biochemistry* 20:3658-64 (1981), which is hereby incorporated by reference in its entirety). Boxes indicate putative 'methyl/phos switch' sites; possible 'modification cassettes' in the tails of H3 and H4 are highlighted.

Only three methyl-marks, Lys14 and Lys36 of H3 and Lys20 of H4, are not next to known or putative phosphorylation sites; however, His18 in H4 could be a phospho-acceptor regulating H4 Lys20 (See FIG. 3). Interestingly, far fewer acetyl-lysine residues than methyl-lysine residues in histones are next to phospho-acceptors (only four out of 14 known acetyl-lysines are neighboring Ser/Thr residues, but four out of six methyl-lysines are next to phospho-acceptors). This situation might reflect the lower stability of acetyl-lysine marks, which are readily erased by histone deacetylases (HDAC), in comparison to less labile methyl-lysine marks. In general, this observation might suggest that stable marks might have coevolved with adjacent flexible marks establishing 'local binary switches' for their regulation.

Survey of all LysSer/Thr or Ser/ThrLys pairs in the major (human) core histones (FIG. 5), identifies an intriguing pattern that suggests an 'order-first' rule. Putative lysine 'switch' sites that have by now been implicated in binding repressive modules (Lys9/Ser10 and Lys27/Ser28 in H3 recruiting HP1 and Polycomb, respectively) directly precede the phospho-acceptor. In contrast, the methyl-mark comes first in the already discussed activating Thr3/Lys4 residue pair in the H3 tail. Based on these observations, the 'lysine-first' 'methyl/phos switches' (LysSer/Thr) suggest a silenced or 'off' state of chromatin. In contrast, 'serine/threonine-first' 'phos/methyl switches' (Ser/ThrLys) may regulate activated or 'on' states of chromatin. The Thr22/Lys23 pair in H3 might, therefore, represent a previously unrecognized activating 'methyl/phos switch'. The situation is, however, less clear at the 'silencing clusters' in H3 (Lys79/Thr80) and H4 (Lys79/Thr80), and methylation at Lys79 might represent an exception to the proposed 'order-first' rule. If it is indeed an 'on' mark reducing SIR repressor binding (Ng et al., "Lysine-79 of Histone H3 is Hypomethylated at Silenced Loci in Yeast and Mammalian Cells: A Potential Mechanism for Position-effect Variegation," *Proc. Natl Acad. Sci. USA* 100:1820-5 (2003), which is hereby incorporated by reference in its entirety), loss of silencing in yeast mutants of H3 Lys79 and the corresponding HMT, Dot1 must be caused by indirect effects (van Leeuwen et al., "Dot1p Modulates Silencing in Yeast by Methylation of the Nucleosome Core," *Cell* 109:745-56 (2002), which is hereby incorporated by reference in their entirety).

The proposed 'order-first' rule might only apply to more-stable marks such as lysine methylation. Acetylation of Lys9 in H3, for example, is well documented. Several studies have shown that acetyl-Lys9 synergizes with phospho-Ser10, and the di-modified, acetyl/phos state of this pair correlates with immediate-early gene activation (Clayton et al., "Phosphoacetylation of Histone H3 on c-fos- and c-jun-associated Nucleosomes Upon Gene Activation," *EMBO J.* 19:3714-26 (2000), which is hereby incorporated by reference in its entirety). However, as indicated earlier, a phospho-switch, proposed to be a 'release button' for methyl-binding effector proteins (FIG. 4), may not be needed to 'eject' acetyl-binding modules (such as bromodomains), as acetyl-marks are easily erased by HDAC activities. Similar considerations might apply to sites of ubiquitination, as deubiquitinating enzymes exist. Yet, Lys119 of H2A precedes Thr120, which would be consistent with this ubiquityl-mark functioning as an 'off'-switch. Indeed, recent work shows, that ubiquitination of H2A Lys119 is enriched in the heterochromatic XY sex body during murine spermatogenesis (Baarends et al., "Histone Ubiquitination and Chromatin Remodeling in Mouse Spermatogenesis," *Dev. Biol.* 207:322-33 (1999), which is hereby incorporated by reference in its entirety). In contrast, Lys120 of H2B is preceded by Thr119, which would be consistent with this ubiquityl-mark functioning as an 'on'-switch. In support, ubiquitination of H2B governs an activating 'trans-histone' regulatory pathway in yeast that involves methylation of Lys4 and Lys79 in H3 (Fischle et al., "Histone and Chromatin Cross-talk," *Curr. Opin. Cell Biol.* 15:172-83 (2003), which is hereby incorporated by reference in its entirety). Moreover, ubiquitinated H2B is only detected in transcriptionally active macronuclei of *Tetrahymena* and is absent from transcriptionally silent micronuclei that contain ubiquitinated H2A (Davie et al., "Timing of the Appearance of Ubiquitinated Histones in Developing New Macronuclei of *Tetrahymena thermophila*," *Biochem. Cell. Biol.* 69:66-71 (1991), which is hereby incorporated by reference in its entirety).

How could the proposed 'order-first' rule of 'lysine-first' ('off') versus 'serine/threonine-first' ('on') switches be implemented? The binding of most modules to their cognate marks is highly asymmetric. For example, the chromodomains of HP1 and Polycomb make contacts to four to six residues N-terminal to the recognized methyl-lysine marks, but 'see' only one residue C-terminal to the modification site (Fischle et al., "Molecular Basis for the Discrimination of Repressive Methyl-Lysine Marks in Histone H3 by Polycomb and HP1 Chromodomains," *Genes Dev.* 17:1870-81 (2003), which is hereby incorporated by reference in its entirety). Similarly, the structure of the bromodomain of Gcn5 bound to the H4 Lys16 acetyl-mark shows major contacts only to the N-terminal face of the binding site. Indeed, asymmetry of binding interfaces is a common phenomenon in cell biology (for example, SH2 domains bind asymmetrically to phosphotyrosine containing sequences) (Pawson et al., "SH2 Domains, Interaction Modules and Cellular Wiring," *Trends Cell Biol.* 11:504-11 (2001), which is hereby incorporated by reference in its entirety). An asymmetric readout of switch-sites by conserved modules could dictate the biology of these post-translational modifications. Modules that read the 'on' switches (like Thr3Lys4$^{methyl}$) or the 'off' switches (like Lys9$^{methyl}$Ser10, Lys27$^{methyl}$Ser28) of the 'order-first' rule might therefore recognize opposed and contrary faces of their cognate binding sites.

Beyond binary switching mechanisms between two neighboring or nearby marks, linear strings of densely clustered modifiable sites in histones might generally not act independently but rather function as discrete information units mediating and relaying different signals. Whereas signature sequence motifs of protein-protein interaction have been defined in many biological pathways, the combination of dense marks in short clusters, situated at strategic locations in the histones, could form defined 'modification cassettes' with distinct biological readouts depending on their modification state (e.g. a 'cassette' of 3 marks could have 23 possible states if each mark can be modified independently).

Short 'cassettes' where at least three out of five sites separated by no more than one residue can be covalently modified are readily spotted in the H3 and H4 tails (see FIG. 3). The stretch between Lys9 and Thr11 of H3, for example, can carry four different covalent marks. Additional clusters of adjacent marks on H3 are centered around Lys4 and Lys27. On the H4 tail, 'cassettes' where single modification sites are separated by only one residue can be found. In H4 of most species, Ser1, Arg3, and Lys5 are well-known sites of phosphorylation, methylation, and acetylation, respectively. Similarly, Lys16 and Lys20, situated more internally in the H4 tail, are sites of acetylation and methylation, respectively, and an older literature suggests that His18 might be an acid-labile phosphorylation site (Fujitaki et al., "Characterization of Chemical and Enzymatic Acid-labile Phosphorylation of Histone H4 Using Phosphorus-31 Nuclear Magnetic Resonance," *Biochemistry* 20:3658-64 (1981), which is hereby incorporated by reference in its entirety).

The modification of adjacent sites within short clusters of accumulated histone modifications will influence the recognition and binding of modules to their cognate mark (see 'local binary switches'). Especially, since the recognition of short clusters of 5-10 amino acids is a hallmark of the interaction of most modules with their target interaction marks (Pawson et al., "SH2 Domains, Interaction Modules and Cellular Wiring," *Trends Cell Biol.* 11:504-11 (2001), which is hereby incorporated by reference in its entirety). Furthermore, modules directly reading complex patterns of marks might exist.

Some putative 'modification cassettes' of major histones are also found in minor histone variants, possibly arguing for conserved functions. For example, the extreme N-terminus of H4 in most species is also found at the very N-terminus of most, but not all, H2A variants (FIG. 6A). In contrast, the stretch [AG-GK . . . ], which marks the beginning of the H2A.Z variant in several species, is identical to the extreme N-terminus of *Tetrahymena* H4. Could the change of Ser1 to Ala1 be linked to the loss of Arg3 in specific members of both H2A and H4 gene families? Perhaps, phosphorylation at Ser1 in H4 or H2A is linked to methylation at nearby Arg3 (or vice versa).

Interestingly, p53 shows features of post-translational modification that are reminiscent of histones. The basic C-terminal region of this tumor suppressor can be phosphorylated and acetylated on multiple sites (FIG. 4B) (Appella et al., "Signaling to p53: Breaking the Posttranslational Modification Code," *Pathol. Biol. (Paris)* 48:227-45 (2000) and Prives et al., "Why is p53 Acetylated?," *Cell* 107:815-8 (2001), which are hereby incorporated by reference in their entirety), and methylation of p53 in this domain is under active investigation. Post-translational modifications at eight out of 13 residues not only give rise to a high density of marks but also to a large number of putative combinations of marks. Similar to histones, some cross-talk between different marks on p53 have been described (i.e. phospho-marks facilitating consecutive acetylation and acetyl-marks possibly interfering with ubiquitination) (Appella et al., "Signaling to p53: Breaking the Posttranslational Modification Code," *Pathol. Biol. (Paris)* 48:227-45 (2000) and Brooks et al., "Ubiquitination, Phosphorylation and Acetylation: The Molecular Basis for p53 Regulation," *Curr. Opin. Cell Biol.* 15:164-71 (2003), which are hereby incorporated by reference in their entirety). However, whereas discrete functions and signaling events have been associated with some marks (i.e. protein stability and DNA binding activity), the biological role of other marks is still debated (Prives et al., "Why is p53 Acetylated?," *Cell* 107:815-8 (2001), which is hereby incorporated by reference in its entirety). Whether aspects of the biology and function of these post-translational marks on p53 could be explained in the context of 'modification cassettes' and/or by switching mechanisms similar to the ones introduced here for histones remains to be determined.

The development of sensitive proteomic approaches will soon lead to the discovery of additional clusters of modifications on other non-histone proteins. Comparison of the sequence motifs of the proposed 'modification cassettes' with other proteins identifies some striking similarities. For example, the extreme N-terminus of most H4s [SGRGK . . . ] is found precisely in the AML/RUNX/RUNT family of transcriptional regulators (FIG. 6B). Similarly, the *Drosophila* H4 N-terminal motif [TGRGK . . . ] is also present in the NRF and MCM4 proteins of higher organisms and at the very N-terminus of *Drosophila* Polycomb (FIG. 6C). While it remains unknown to what extent covalent modifications exist in these short clusters, these conserved motifs could represent discrete information units with yet unknown regulatory function. Whether the general concepts presented here for histones might ultimately be applicable to other proteins and signaling cascades remains an intriguing possibility.

EXAMPLES

Example 1

Lys9-Ser10 Binary Switch on Histone H3

While some histone modifications (e.g., acetylation, phosphorylation) are highly reversible, others (e.g., methylation) are more static and mechanisms for their removal are not known. Whereas this feature makes such marks perfectly suited for mediating inheritable (=epigenetic) features of chromatin, the means of controlling the functional readout of stable methyl-histone marks are unsolved. Examination of the three-dimensional structures of the HP1 and Polycomb chromodomain methyl-peptide complexes suggested that phosphorylation of serine residues adjacent to the target methyl-lysine sites could result in loss of effector binding. In fact, binding of HP1 to a dually modified, trimethyl-lysine 9 phospho-serine 10 H3 peptide, is significantly reduced. Mass spectrometric analysis of cellular histone samples indicates the existence of this dual modification pattern on H3 in vivo and dynamic phosphorylation and dephosphorylation of serine 10 adjacent to the methyl-lysine 9 site could be demonstrated. Importantly, phosphorylation of serine 10 by H3 kinases results in effective release of the HP1 effector module from its target methyl-lysine 9 site. Based on these novel findings, 'binary methyl-phos switches' are believed to exist, which could explain the unsolved puzzle of dynamic readout of non-removable methyl-histone marks. According to this model, the readout of a stable histone mark that engages an effector module is directly controlled by neighboring or adjacent reversible modification(s) leading to consecutive loss of binding to that factor. 'Binary switches' could be a major instrument for the regulation of recruitment and binding of effector proteins to histone (and generally other protein) marks by combining the crucial need of flexible readout of histone modifications with the requirement for inheritable marks in chromatin to direct the functionality of a cells genome.

As described above, dynamic readout of otherwise static histone methylation marks can be achieved by 'local switching' mechanisms. According to this mechanism, phosphorylation of a site adjacent to (or nearby) a methyl-mark that engages an effector module could lead to consecutive loss of binding to that factor. Such 'binary switches' can add an important dynamic nature to the readout of marks that themselves have very low turnover rates and suggest that 'methyl/phos switching' could be a widespread mechanism regulating the binding and release of effector modules to more stable methyl-marks. Here, analysis of such a 'binary methyl-phos' switch shows its ability to regulate the binding and release of heterochromatin protein 1 (HP1) to histone H3.

FIG. 7A shows the sequence of the N-terminus (residues 1-30) of histone H3. Methylation (M) of Lys 9 is known as a hallmark of heterochromatin, whereas Ser 10 is known to be phosphorylated (P) during mitosis and during immediate early gene signaling.

Figure 7B:
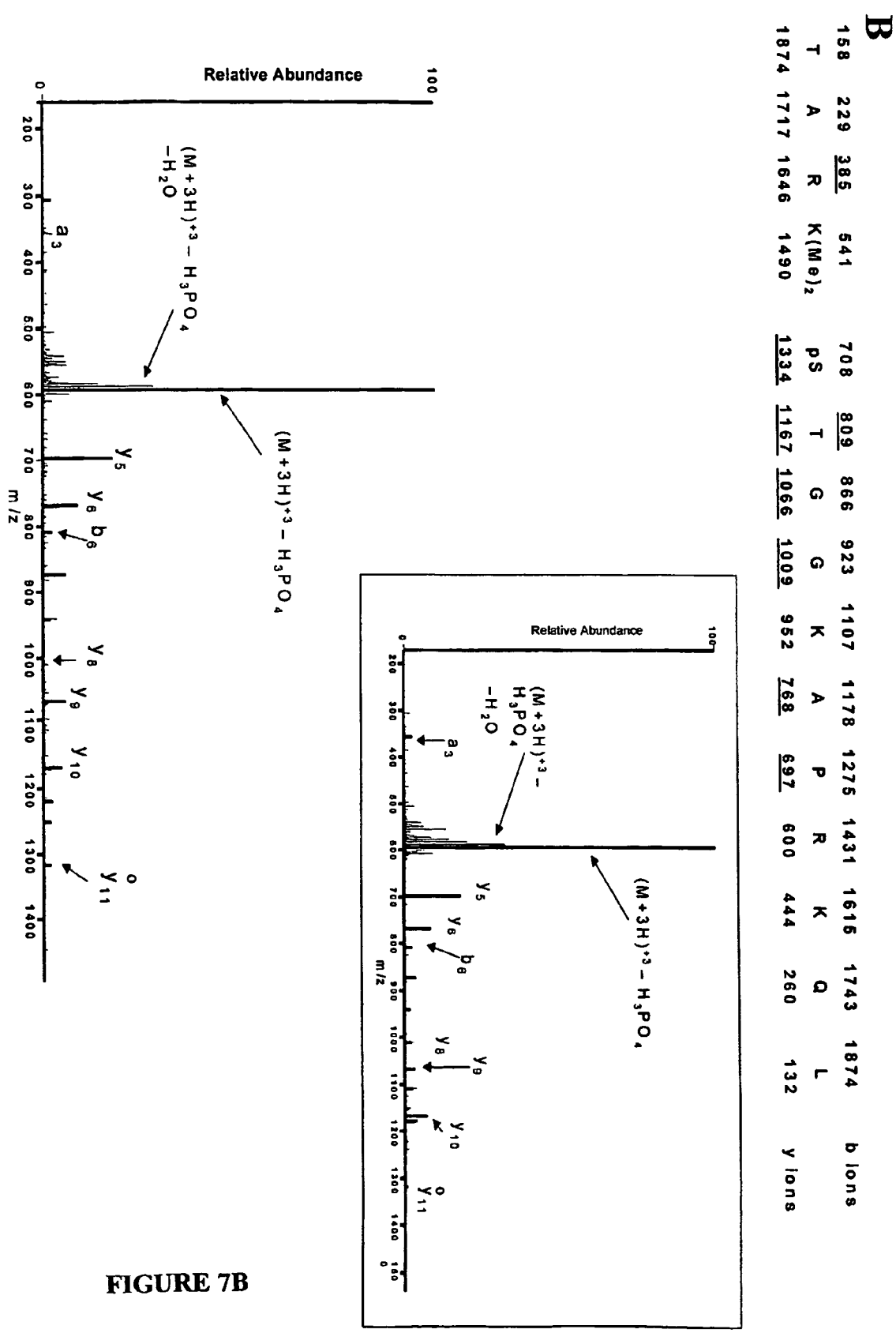

HeLa cells were synchronized by double thymidine blocking. Total histones were acid extracted and H3 was isolated by reversed phase (C8) chromatography. After treatment with propionic anhydride and limited tryptic digestion, an H3 peptide (residues 6-20) was isolated and analyzed by MS/MS. The predicted masses for singly charged fragment ions of type-b (acylium ions containing the N-terminus) and type-y (truncated peptides containing the C-terminus) are denoted above and below the peptide sequence. Ions observed in the spectra of the isolated peptide are underlined. The MS/MS spectrum recorded on a corresponding synthetic peptide, derivatized with propionic anhydride and containing the me3K9pS10 dual modification is shown in the inlet. FIG. 7B shows the mass spec identification of the dual H3-me3K9pS10 modification pattern in HeLa cells.

Example 2

Analysis with Antibodies Raised Against the H3 Peptide Containing Lys9 and Ser10

Rabbit polyclonal antibodies were raised against a synthetic peptide corresponding to the H3 tail tri-methylated at Lys9 and phosphorylated at Ser10 (me 3k9p S10).

Dilution series of H3 peptides containing the indicated modifications were spotted onto PVDF membranes and probed with anti-H3-me3K9pS10 antibodies (1:500 dilution). Peptides were visualized using a goat anti-rabbit secondary antibody conjugated to HRP and a chemiluminescence detection system. FIG. 8A shows a peptide dot blot analysis.

HeLa acid extracts were resolved by electrophoresis, transferred to nitrocellulose, and probed with anti-H3-me3K9pS10 antibodies (1:20,000 dilution, Lane 1) or anti-H3-me3K9pS10 antibodies pre-absorbed with 1 µM histone H3 peptides containing the indicated modifications. Proteins were visualized using a goat anti-rabbit secondary antibody conjugated to HRP and a chemiluminescence detection system. FIG. 8B shows a peptide inhibition analysis.

Different amounts of H3 peptides containing the indicated modifications were adsorbed to plastic dishes and probed with anti-H3-me3K9pS10 antibodies (1:15,000 dilution). Peptides were quantified using a goat anti-rabbit secondary antibody conjugated to HRP with OPD as substrate. Absorbances at 490 nm were read in a plate reader. FIG. 8C shows ELISA results.

Example 3

Phosphorylation of the H3 Tail

The specified peptides corresponding to the N-terminus of H3 were incubated with the indicated recombinant kinases in the presence of [32P]-ATP. Aliquots of the reactions were taken at different time intervals and stopped by the addition of acetic acid (20% final). Aliquots were spotted onto phosphocellulose (P81) filters. After intensive washing, incorporation of [32P] into the H3 peptides was measured by scintillation counting.

Figure 9:
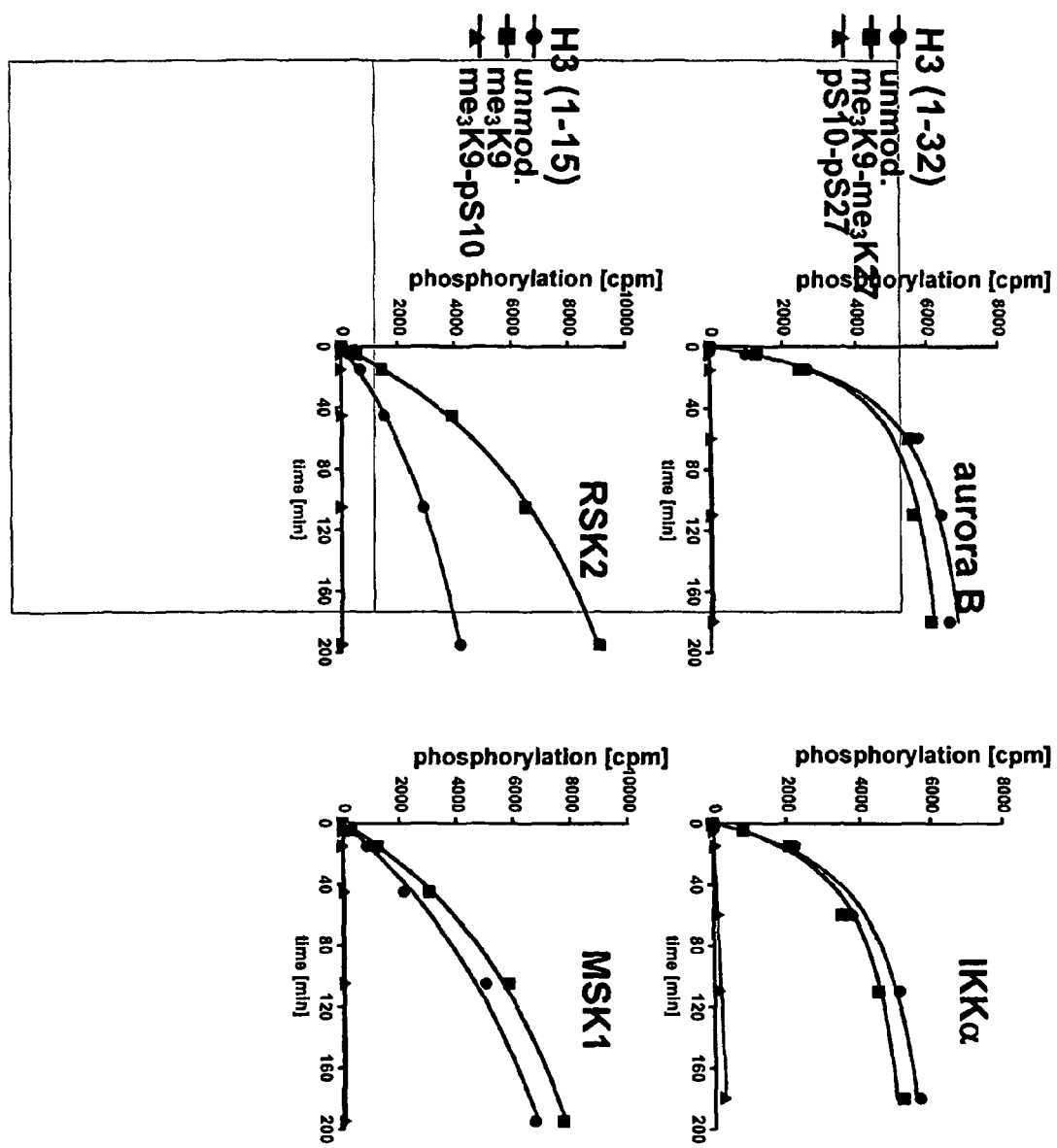
FIG. 9 shows the phosphorylation of the H3 tail methylated on Lys 9 by different histone kinases.

As shown in FIG. 9, all values were corrected for kinase auto-phosphorylation as well as unspecific filter binding of substrate.

Example 4

Impairment of HP1 Binding to H3 Tail Methylated at Lys9

Figure 10:
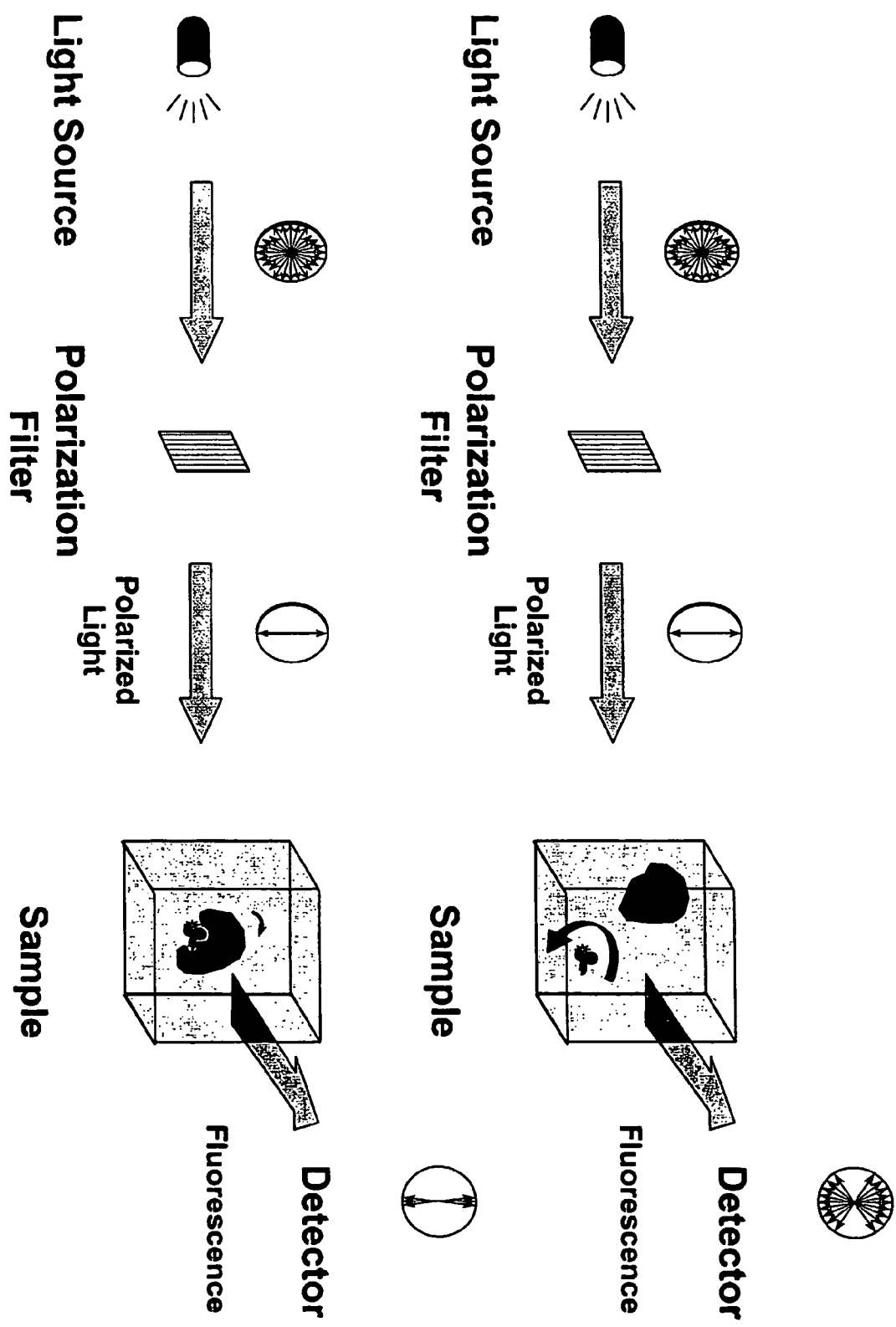
FIG. 10 shows the schematic depiction of binding assays using fluorescence polarization. Note, in this system all measurements are done at binding equilibrium.

Using the binding assay shown schematically in FIG. 10, binding studies were carried out using fluorescence polarization.

Figure 11:
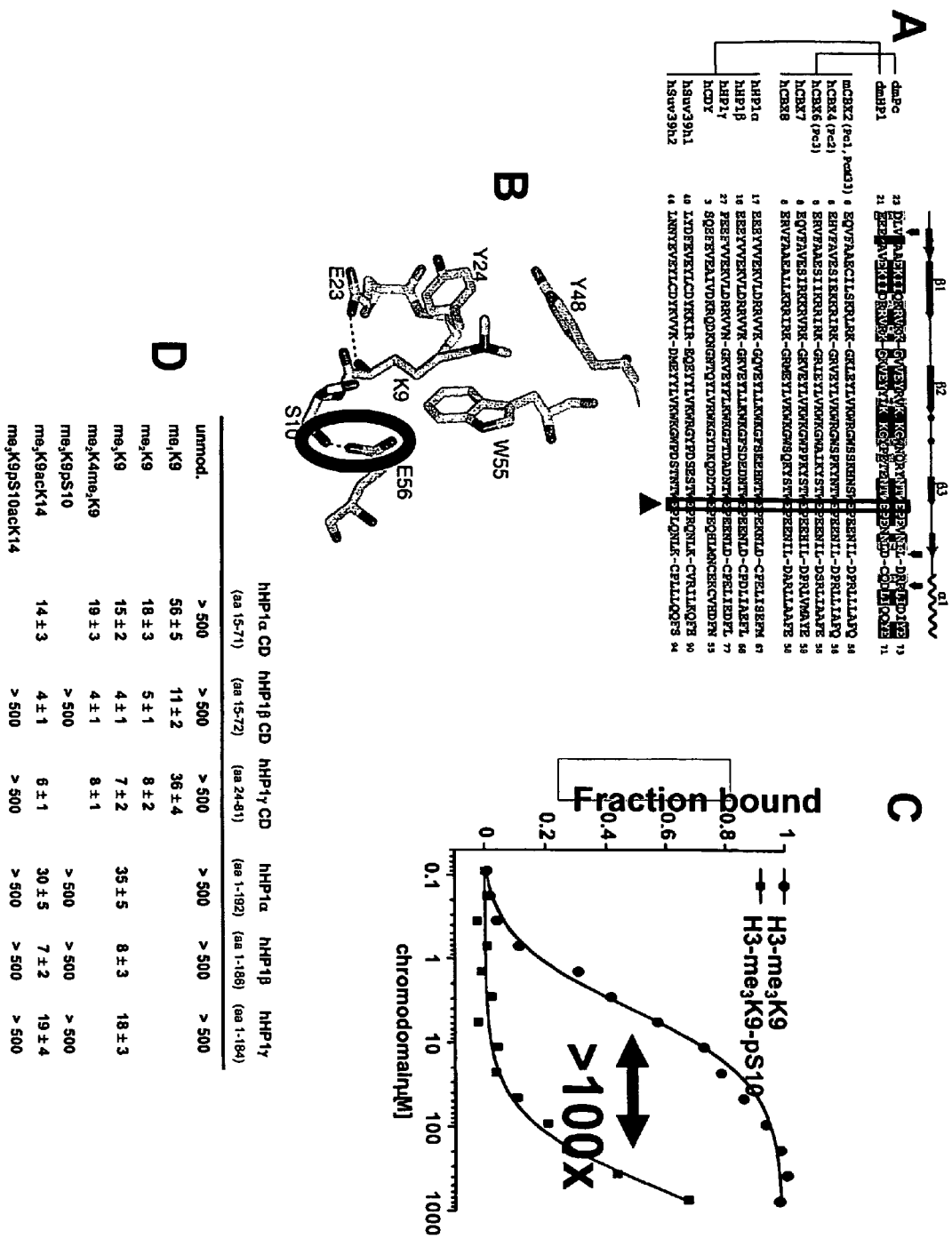
FIGS. 11A-D show binding of HP1 to the H3 tail methylated at Lys 9 and phosphorylated at Ser 10 is impaired.

FIG. 11A shows the alignment of different chromodomains with affinity for histone methyl-marks. A conserved Glu residue predicted to make contact to the H3 tail exiting the chromodomain binding groove is highlighted.

FIG. 11B shows a close-up view of residues crucial for the binding of the HP1 chromodomain to an H3-meK9 peptide. Three aromatic residues in HP1 (two tyrosines and one tryptophan) form an aromatic cage that engages the methyl-groups in hydrophobic van der Waals interactions. A conserved Glu residue (E56) forms a hydrogen bond with the Ser C-terminal to the methylated Lys residue (encircled).

Binding of HP1 to H3-me3K9 and H3-me3K9pS10 peptides was compared by fluorescence anisotropy measurements. FIG. 11C shows the binding of HP1 to H3-me3K9 is impaired when Ser 10 is phosphorylated. Data points represent the average of three independent experiments.

FIG. 11D shows the binding affinities of recombinant human HP1 polypeptides for differentially modified H3 peptides. Single site-binding constants (KD in mM) for H3 tail peptides containing the indicated modifications were obtained using fluorescence polarization measurements. For each peptide, binding curves with the titrated recombinant proteins were analyzed by non-linear least squares fitting using the equation A=[Af−(Ab−Af)]×[chromodomain]/(KD+[chromodomain]), where A represents the measured anisotropy at a given protein concentration and Af and Ab correspond to the anisotropy of the free and bound peptides, respectively. Values represent the averages of at least three independent experiments.

HP1 (100 mM) was mixed with an fluorescin labeled H3-me3K9 peptide (200 nM) and the fluorescence polarization was recorded. Increasing amounts of the indicated unlabeled peptides were added and the fluorescence polarization was recorded within 10 sec after mixing, as shown on FIG. 12. The mean fraction bound of fluorescinated peptide was calculated for each titration. Values plotted represent the average of three independent readings.

Example 5

In Vitro Switching

Having established the occurrence of the dual H3-me3k9pS10 modification pattern in vivo as well as measuring the largely different binding affinities of HP1 for the H3-me3K9 and H3-me3K9pS10 modified histone H3 tails in vitro, it was decided to analyze if HP1 could indeed be displaced from binding to the H3 tail methylated on Lys 9 by phosphorylation of Ser 10. To this end, the in vitro binding system using fluorescinated peptides and recombinant HP1 chromodomain proteins was used. 'Switching' was achieved by using recombinant (and activated) MSK1 as a established histone H3 Ser 10 kinase and PP1 (rabbit skeletal muscle) as a established phospho-Ser 10 phosphatase. The change of binding behavior was analyzed by fluorescence polarization measurements. Recently, a mass spectrometric system was established to follow the progression of the enzymatic reaction simultaneously to the gain or loss of binding in a single tube assay.

As shown in FIG. 13A, the chromodomain of HP1 was incubated with a fluorescinated H3-me3K9 peptide (200 nM). After addition of MSK1 and ATP (ON), the fluorescence polarization of a dilution series of HP1 was recorded. The corresponding values of HP1 bound to a H3-me3K9 or a H3-me3K9pS10 peptide are blotted for comparison.

FIG. 13B shows the phosphorylation of the recombinant (10×HIS tagged) HP1 chromodomain polypeptide does not interfere with binding to a H3-me3K9 peptide. HP1 was incubated with active or inactivated (✝) MSK1 and ATP (ON, 30° C.). Samples of the reaction were run on SDS-PAGE (Coomassie). The asterisk denotes the slower migrating phosphorylated 10×HIS-HP1 polypeptide. Additional samples of each reaction were spiked with fresh active MSK1 and [32P]-ATP. After incubation at 30° C. for 1 hr, reactions were run on SDS-PAGE and analyzed by autoradiography (32P). The bulk of the pre-phosphorylated HP1 protein was analyzed for binding to a H3-me3K9 peptide by fluorescence anisotropy measurements.

Figure 13C:
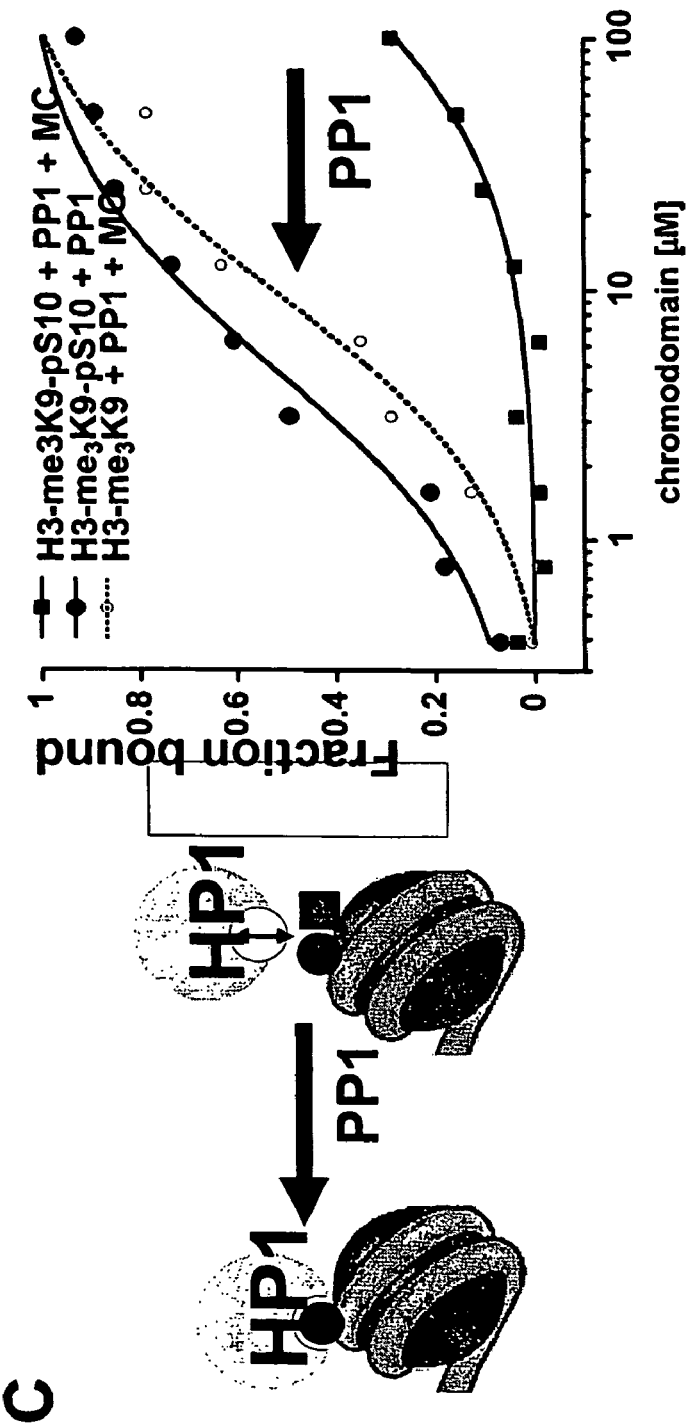

FIG. 13C shows the dephosphorylation of a H3-me3K9pS10 peptide by PP1 results in HP1 binding similar to a H3-me3K9 peptide. The chromodomain of HP1 was incubated with a fluorescinated H3-me3K9pS10 peptide (200 nM). After addition of PP1 (3 hrs), the fluorescence polarization of a dilution series of HP1 was recorded. The corresponding values of HP1 bound to a H3-me3K9 or a H3-me3K9pS10 peptide are blotted for comparison. Microcystin LR (MC, 100 nM) was added to inhibit PP1 in the indicated reactions.

As shown in FIG. 13D, the phosphorylation of the 10×HIS-HP1 polypeptide occurs in the linker region. The indicated recombinant 6×HIS and 10×HIS HP1 polypeptides were incubated with MSK1 and [32P]-ATP (1 hr, 30° C.). Reactions were run on SDS-PAGE, stained with Coomassie and analyzed by autoradiography (32P).

Figures 14A, 14C:
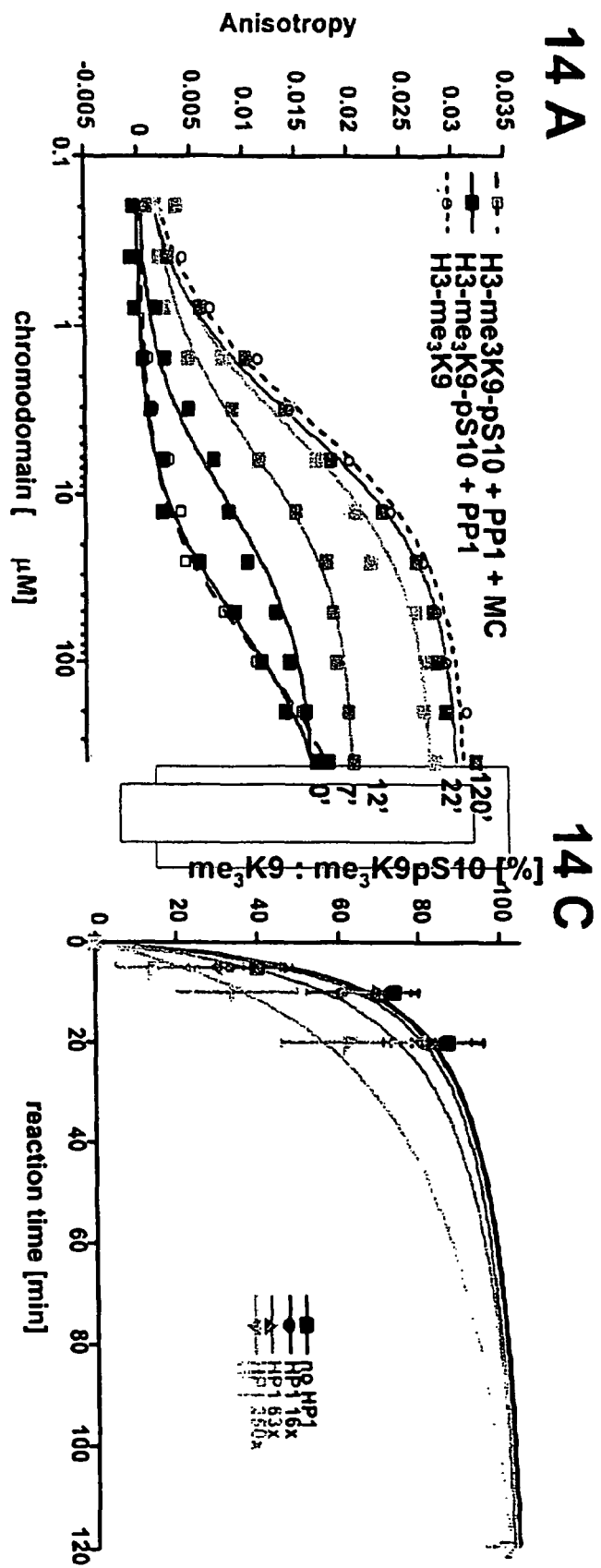

FIG. 14A shows the recombinant chromodomain of HP1 was incubated with a fluorescinated H3-me3K9pS10 peptide (400 nM). Fluorescence polarization was recorded before (0') and after the addition of PP1 (7', 12', 22', 120'). Recordings of the corresponding reactions but in the presence of 100 nM microcystin LR (MC) as well as for the unphosphorylated H3-me3K9 peptide are shown as references.

Figure 14B:
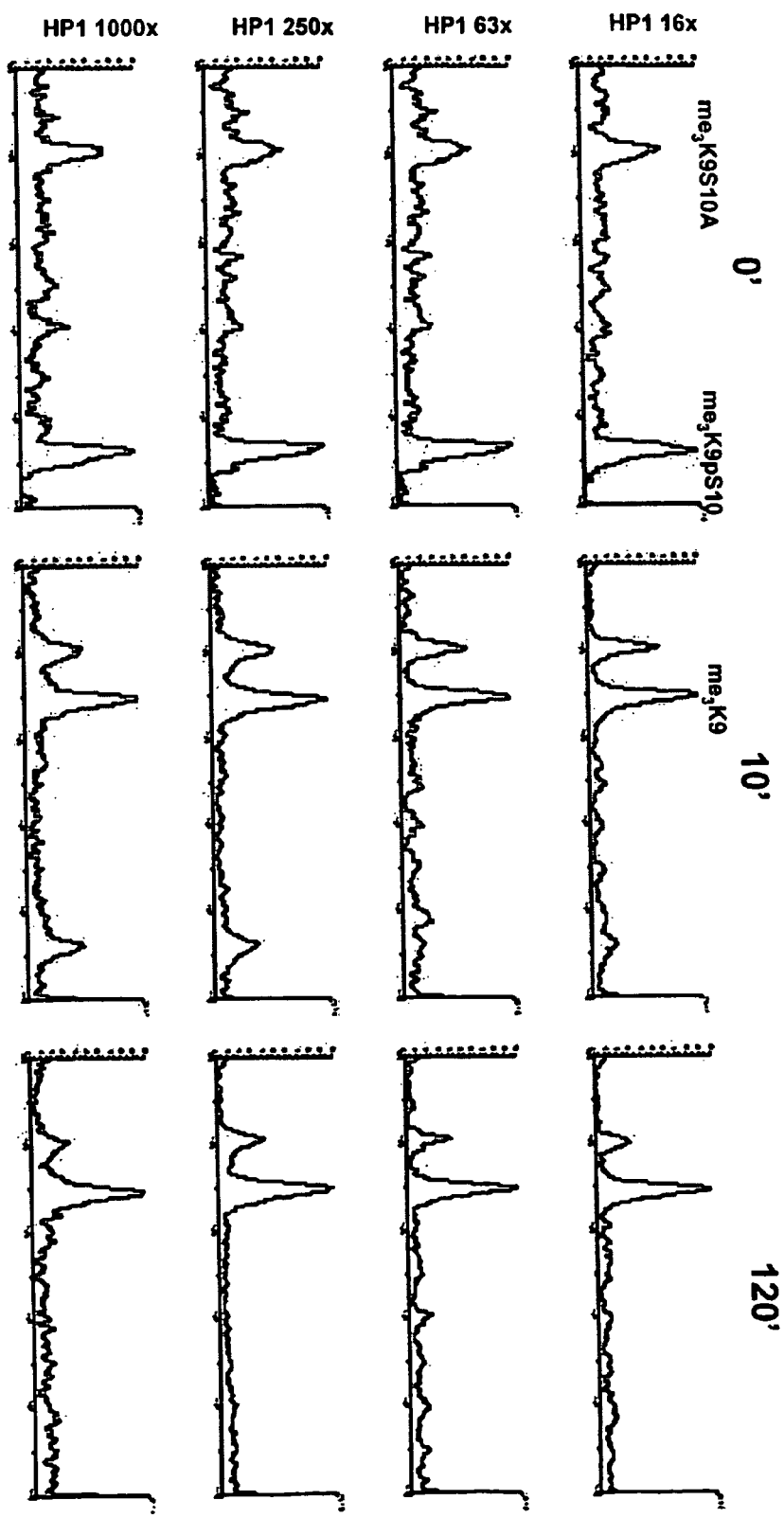

FIG. 14B is a mass spectrometirc analysis of the progression of the switching reaction. Samples of the dephosphorylation reactions were taken at different time intervals and stopped by the addition of one vol. 0.5% TFA. Mass spectra were recorded on a MALDI TOF instrument (Voyager RP STR) in linear mode with a-cyano-hydroxy cinnamic acid as matrix. Each spectrum corresponds to 100 accumulated shots. Exemplary spectra of the progression of the dephosphorylation reaction at different HP1 concentrations are shown (1×=400 nM peptide in the reaction).

FIG. 14C shows a kinetic analysis of the dephosphorylation of the H3-me3K9pS10 peptide in the absence (no HP1) and presence of different amounts of HP1. The relative amounts of H3-me3K9pS10 and H3-me3K9 peptides in the reactions were determined in relation to an added constant amount of H3-me3K9S10A peptide. Each measurement was the average of ten spectra collected at ten different spots with 100 shots per position.

In FIG. 14D, aliquots of the reactions were run on SDS-PAGE and stained with Coomassie. The arrows indicate the running position of the 6×HIS HP1b CD polypeptide (lower) as well as the PP1 polypeptide (upper). The asterisk denotes a dimer form of HP1 that was also observed in MALDI TOF mass spectra (<5% of total HP1 in the reaction).

The in vitro analysis of the binding of HP1 to the H3 tail methylated on Lys 9 in dependence of Ser 10 phosphorylation shows that binary 'methyl-phos switching' is indeed possible and could be a general mechanism regulating the binding and release of effector proteins to otherwise stable histone modification marks. It has also been shown that the dual H3-me3K9pS10 modification pattern occurs in vivo. The pre-mitotic occurrence of this dual mark is in good agreement with the known displacement of HP1 from chromatin at the onset of mitosis.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed:

1. A method comprising:
   a) providing a candidate compound;
   b) providing a chromatin binding protein;
   c) contacting i) the candidate compound and ii) the chromatin binding protein with iii) a histone comprising a serine or threonine within three amino acids from an arginine amino acid capable of being methylated or a lysine amino acid capable of being methylated, acetylated, ubiquitinated, or SUMOylated;
   d) measuring both i) the binding of the chromatin binding protein to the histone and ii) phosphorylation of the histone, in the presence and absence of the candidate compound; and
   e) identifying, based on said measuring, the candidate compound that either i) decreases the binding of the chromatin binding protein to the histone and increases the serine or threonine phosphorylation of the histone or ii) increases the binding of the chromatin binding protein to the histone and decreases the serine or threonine phosphorylation of the histone, thereby identifying the candidate compound which increases or decreases the binding of the chromatin binding protein to the histone.

2. The method according to claim 1, wherein the serine or threonine on the histone is a phosphorylated serine or threonine and the binding of the chromatin binding protein is decreased.

3. The method according to claim 1, wherein the amino acid is lysine.

4. The method according to claim 1, wherein the arginine or lysine is methylated.

5. The method according to claim 1, wherein the serine or threonine is adjacent to the amino acid.

* * * * *